US008067538B2

(12) United States Patent
Kondo

(10) Patent No.: US 8,067,538 B2
(45) Date of Patent: Nov. 29, 2011

(54) GENE RELATED TO GROWTH PROMOTING FUNCTION OF ACETIC ACID BACTERIUM, ACETIC ACID BACTERIUM BRED USING THE GENE AND METHOD FOR PRODUCING VINEGAR USING THE ACETIC ACID BACTERIUM

(75) Inventor: Tomoo Kondo, Chiryu (JP)

(73) Assignee: Mizkan Group Corporation (JP)

( * ) Notice: Subject to any disclaimer, the term of this patent is extended or adjusted under 35 U.S.C. 154(b) by 449 days.

(21) Appl. No.: 12/281,147

(22) PCT Filed: Mar. 1, 2007

(86) PCT No.: PCT/JP2007/053901
§ 371 (c)(1),
(2), (4) Date: Sep. 8, 2008

(87) PCT Pub. No.: WO2007/100036
PCT Pub. Date: Sep. 7, 2007

(65) Prior Publication Data
US 2010/0240869 A1    Sep. 23, 2010

(51) Int. Cl.
| | |
|---|---|
| A61K 38/00 | (2006.01) |
| A61K 39/00 | (2006.01) |
| A61K 39/02 | (2006.01) |
| C07K 14/00 | (2006.01) |
| C07K 17/00 | (2006.01) |
| C07K 16/00 | (2006.01) |
| C07K 2/00 | (2006.01) |
| C07K 4/00 | (2006.01) |
| C07K 5/00 | (2006.01) |
| C07K 7/00 | (2006.01) |
| C07H 21/04 | (2006.01) |
| C07H 21/02 | (2006.01) |
| C12N 1/12 | (2006.01) |
| C12N 1/20 | (2006.01) |

(52) U.S. Cl. ............... 530/350; 424/185.1; 424/234.1; 536/23.1; 536/23.7; 435/252.3

(58) Field of Classification Search .................. None
See application file for complete search history.

(56) References Cited

U.S. PATENT DOCUMENTS

| | | | | |
|---|---|---|---|---|
| 6,562,958 | B1 * | 5/2003 | Breton et al. ............... | 536/23.7 |
| 7,256,025 | B2 * | 8/2007 | Goto ............................. | 435/140 |
| 7,354,751 | B2 * | 4/2008 | Nakano ........................ | 435/189 |
| 7,446,192 | B2 * | 11/2008 | Goto et al. ................... | 536/23.7 |
| 7,541,491 | B2 * | 6/2009 | Nakano ........................ | 562/536 |
| 2006/0228445 | A1 * | 10/2006 | Nakano ........................ | 426/17 |
| 2006/0286652 | A1 * | 12/2006 | Goto ............................. | 435/140 |
| 2007/0026104 | A1 * | 2/2007 | Nakano ........................ | 426/17 |
| 2010/0105117 | A1 * | 4/2010 | Iida ............................... | 435/140 |
| 2010/0137641 | A1 * | 6/2010 | Iida ............................... | 562/607 |
| 2010/0159541 | A1 * | 6/2010 | Iida ............................... | 435/140 |
| 2010/0240869 | A1 * | 9/2010 | Kondo .......................... | 530/350 |

FOREIGN PATENT DOCUMENTS

| | | |
|---|---|---|
| EP | 1 489 182 | 12/2004 |
| EP | 1 602 728 | 12/2005 |
| EP | 1 642 977 | 4/2006 |
| JP | 60180581 A * | 9/1985 |
| JP | 2004305209 A * | 11/2004 |
| JP | 2006230329 A * | 9/2006 |
| JP | 2006246701 A * | 9/2006 |
| WO | WO03/078635 | 9/2003 |
| WO | WO2004/081216 | 9/2004 |
| WO | WO2005/001095 | 1/2005 |
| WO | WO 2007/100036 A1 * | 9/2007 |

OTHER PUBLICATIONS

Bertalan et al, BMC Genomics, Sep. 23, 2009, 10:450.*
Greenspan et al, Nature Biotechnology 7: 936-937, 1999.*
Deppenmeier et al, Appl. Microbiol. Biotechnol., 2002, 60:233-242.*
Deppenmeier et al, J. Mol. Microbiol. and Biotechnol., 2009, 16:69-80.*
Bixler et al, Synthetic Vaccines, vol. 1, 1987, pp. 39-71.*
Thomas E. Creighton, in his book Protein Structure: A Practical Approach, 1989; pp. 184-186.* Prust et al., "Complete Genome Sequence of the Acetic Acid Bacterium Gluconbacter Oxydans," Nature Biotechnology, vol. 23, No. 2, pp. 195-200, Feb. 2005.
Database GenBank [online], Accession No. CP000009, <<http://www.ncbi.nlm.nih.gov/entrez/viewer.fcgi?val=58000905&from=963068&to=963553&view=gbwithparts>> Feb. 15, 2005 uploaded, retrieved on May 23, 2007, Definition: Gluconobacter Oxydans 621H, complete genome.

* cited by examiner

*Primary Examiner* — Nita M Minnifield
(74) *Attorney, Agent, or Firm* — Kenneth H. Sonnenfeld; Margaret B. Brivanlou; King & Spalding LLP

(57) ABSTRACT

The present invention is to obtain a novel gene that encodes a protein having a function of promoting acetic acid bacterial growth in the presence of a high concentration of acetic acid; to enhance acetic acid bacteria's function of promoting growth and thereby to develop acetic acid bacteria with an improved fermentation ability in the presence of a high concentration of acetic acid; and to provide a method for efficiently producing vinegar that contains a high concentration of acetic acid in a short time using the acetic acid bacterium. A novel gene having a function of improving the function of promoting growth at a practical level was cloned from acetic acid bacteria for practical use, belonging to the genus *Gluconacetobacter*, by a method comprising exposing acetic acid bacterial lysate to the presence of a high concentration of acetic acid; obtaining a gene of a protein that was not insolubilized but remained soluble; and thereby obtaining a gene having a function of promoting acetic acid bacterial growth in the presence of acetic acid. When cultured in the presence of acetic acid and ethanol, a transformant of acetic acid bacteria transformed with the gene was confirmed to have a significant effect of promoting growth.

5 Claims, 11 Drawing Sheets

[Fig. 1]

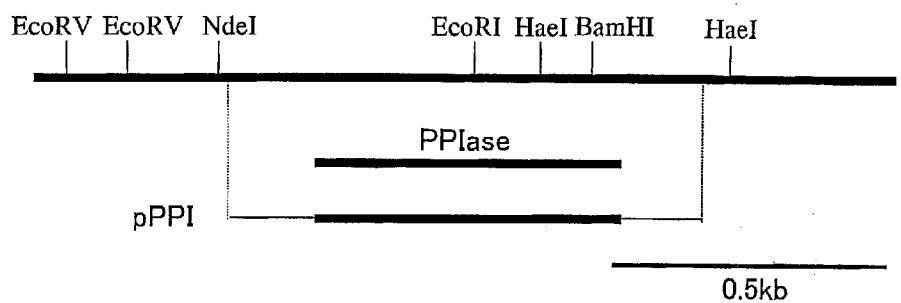

[Fig. 2]

```
MetAspArgGlyArgLeuSerGlyProVal      10
ProProThrLeuHisPheThrLysArgIle      20
ThrMetSerAlaThrGluAsnLysSerAsp      30
LeuIleAsnMetAspLeuLysThrGlyArg      40
ValValIleArgLeuArgProAspLeuAla      50
ProLeuAlaAlaGluArgIleArgThrLeu      60
SerAlaGluGlyPheTyrAspAsnThrPro      70
PheHisArgValIleHisGlyPheMetAla      80
GlnGlyGlyAspProThrGlyThrGlyThr      90
SerGlySerLysLeuProAspLeuLysAla     100
GluPheThrAsnLysAlaLysPheGluArg     110
GlyThrValGlyMetAlaArgThrMetAsn     120
ProAspSerAlaAsnSerGlnPhePheIle     130
MetPheGluProSerProHisIleAspGly     140
GlnTyrThrIleValGlyGlnValIleGlu     150
GlyMetAspHisIleAspLysValLysArg     160
GlyAlaGlyGlnSerGlyMetValGlnAsp     170
ProAspArgIleIleLysMetArgProAla     180
AspAlaGluAla                       184
```

[Fig. 3]
5'-CCCGGGGGTTGCGGATTTCGAATACGAGAACC-3'

[Fig. 4]
5'-GGGCCCGGAAACCGTGGCGTTACACCTTGGG-3'

[Fig. 5]

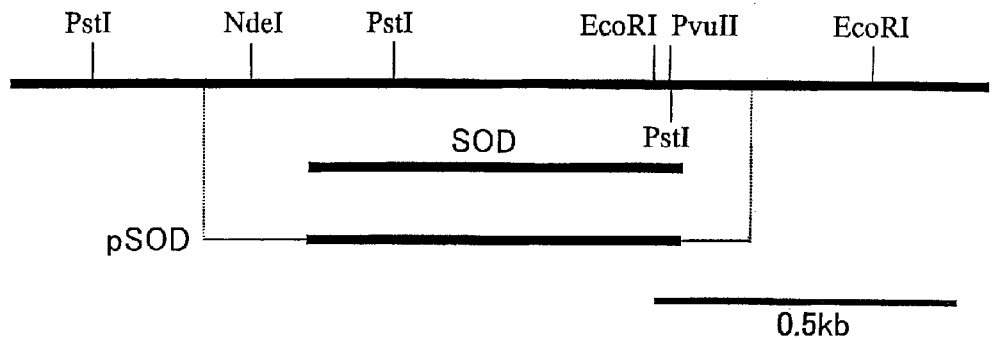

[Fig. 6]

```
MetAlaPheGluLeuProSerLeuProPhe      10
AlaTyrAsnAlaLeuAlaAsnArgGlyMet      20
CysGlnGluThrLeuGluLeuHisHisAsp      30
LysHisHisGlnAlaTyrValThrAlaLeu      40
AsnGlyPheValGluSerLysProGluLeu      50
GlnGlyLysSerLeuGluGluIleIleLeu      60
MetValLysGlyLysProAspMetAlaPro      70
ValPheAsnAsnAlaGlyGlnHisTrpAsn      80
HisIleLeuPheTrpGlnAsnLeuAlaPro      90
LysGlyGlyGluIleProHisAlaLeuSer     100
LysLysLeuValGluAspPheGlyThrIle     110
GluLysPheLysAlaAspPheLysAlaAla     120
AlaAlaSerGlnPheGlySerGlyTrpAla     130
TrpLeuValLeuGlySerAspGlyLysLeu     140
LysValThrLysThrAlaAsnGlySerAsn     150
ProLeuAlaGluGlyGlnGlyLysValLeu     160
LeuGlyLeuAspValTrpGluHisSerTyr     170
TyrLeuAspPheArgAsnArgArgProAsp     180
TyrIleThrAsnTyrLeuAspLysLeuAla     190
AsnTyrGluPheAlaGluAlaGlnLeuGln     200
SerAla                             202
```

[Fig. 7]

5'-CCCGGGAACAGGGCGCAGAAAAAGCGGTCGG-3'

[Fig. 8]

5'-GGGCCCCCCGAGACGCGTGGCATGACGCTGG-3'

[Fig. 9]

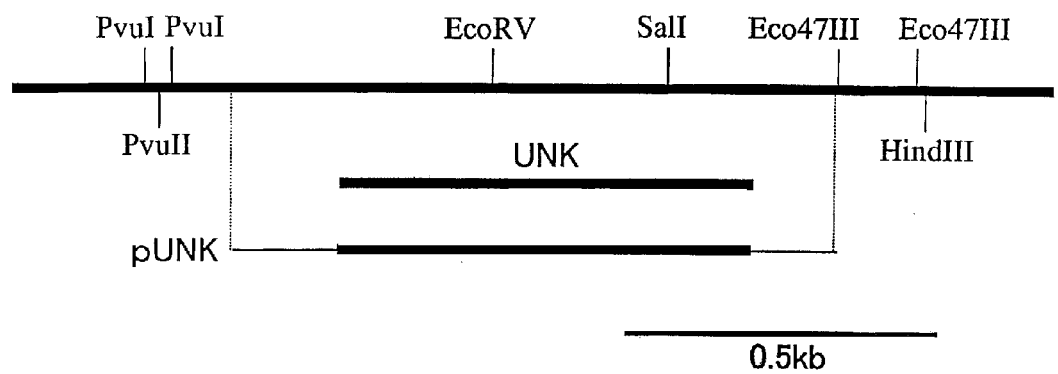

[Fig. 10]

```
MetSerTyrValAspProAlaTrpTyrVal      10
ValAlaAspAsnIleHisAlaArgIleLeu      20
LysHisGlyGluHisGlyLeuAlaThrPhe      30
GluHisLeuLysSerAspAspAlaLysGly      40
MetAspAlaProArgAsnGlyAlaTyrGly      50
LysValIleAlaGluPheLeuAsnThrVal      60
ValArgGlnLysLysAlaProAlaIleAla      70
IleAlaAlaProGlyAspValMetHisGln      80
IleArgAlaHisLeuAspValHisThrArg      90
AlaLeuValValLysGluLeuGluArgAsp     100
LeuThrAsnThrProAspHisGluLeuAla     110
LysHisPheAspIleProAlaThrGlyTrp     120
ProLeuProAsnAlaGly
```

[Fig. 11]

5'-CCCGGGGGCCTGCTGGACCGCGTGCGCTTCC-3'

[Fig. 12]

5'-GGGCCCCGGAAACCGGAGGCATGGGCACCGC-3'

[Fig. 13]

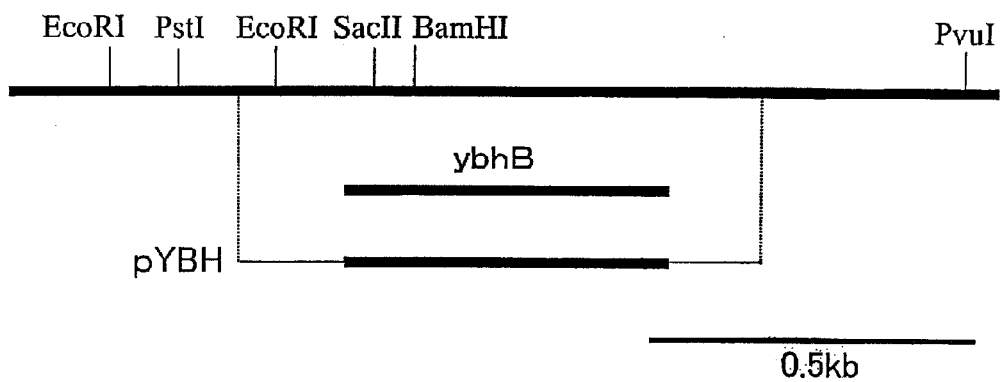

[Fig. 14]

```
MetThrPheThrLeuThrSerArgSerPhe      10
HisAspGlyAspArgLeuProAlaAlaGln      20
ValPheAspGlyMetGlyTyrSerGlyGly      30
AsnIleSerProProLeuAlaTrpGlnAsp      40
ProProAlaGlyThrLysSerPheAlaIle      50
ThrMetTyrAspProAspAlaProThrGly      60
SerGlyTrpTrpHisTrpValValIleAsn      70
IleProAlaThrValSerSerLeuProAla      80
GlyAlaGlySerGlyAspAsnAspLeuPro      90
GluHisAlaGluMetThrArgThrAspPhe     100
GlyGlyAsnValTyrGlyGlyAlaAlaPro     110
ProProGlyProAspHisHisTyrIlePhe     120
ThrIleHisAlaLeuAspIleGluArgIle     130
GluLeuProAsnAspAlaSerGlyAlaMet     140
ValGlyPheValIleAsnGlnHisSerLeu     150
GlySerAlaLysLeuThrAlaValPheGly     160
LysGlnProLys                       164
```

[Fig. 15]

5'-CCCGGGGGTGCTGGAATCGGTCGAGGAAAAGG-3'

[Fig. 16]

5'-GGGCCCGGTGTCCGGGTAACGGAGGGACCGG-3'

[Fig. 17]

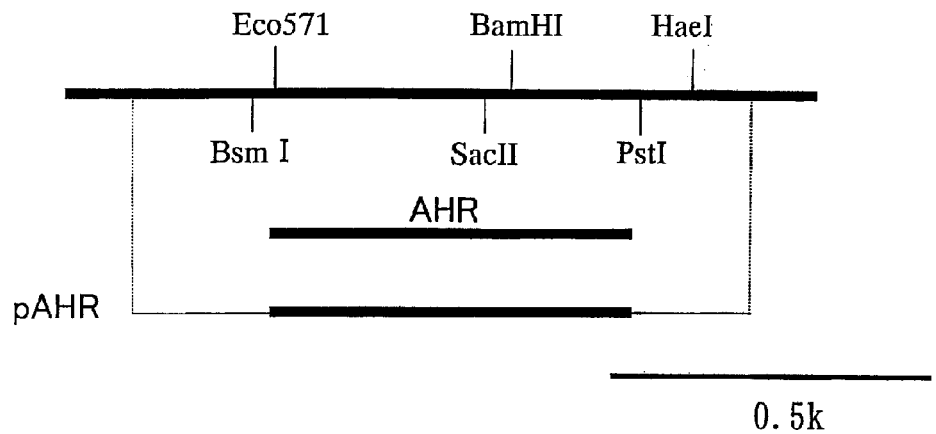

[Fig. 18]

```
MetAlaArgIleAsnSerSerLeuLysPro      10
PheGluThrAspAlaPheHisAsnGlyLys      20
PheIleLysValSerAspAlaAspValLys      30
GlyLysTrpSerValPhePhePheTyrPro      40
AlaAspPheThrPheValCysProThrGlu      50
LeuGluAspLeuAlaGluAsnTyrGluThr      60
PheGlnLysLeuGlyValGluIleTyrSer      70
ValSerThrAspLysHisPheThrHisLys      80
AlaTrpHisAspThrSerProAlaIleSer      90
LysIleLysPheValMetLeuGlyAspPro     100
ThrAlaHisIleAlaArgAsnPheAspVal     110
TyrIleGluGluAlaGlyValAlaAspArg     120
GlyThrPheLeuIleAspProGluGlyArg     130
IleGlnTyrIleGluIleThrAlaGlySer     140
ValGlyArgSerAlaAlaGluLeuIleAla     150
LysIleGluAlaAlaGlnTyrValAlaSer     160
HisProGlyGluValCysProAlaLysTrp     170
LysGluGlyGlyAlaThrLeuThrProSer     180
LeuAspLeuValGlyLysIle
```

[Fig. 19]
5'-CCCGGGGCCACCACATATTCGATGTCGCGCA-3'

[Fig. 20]
5'-GGGCCCCAGGAGTTCATGCATCTCACGCGAA-3'

[Fig. 21]

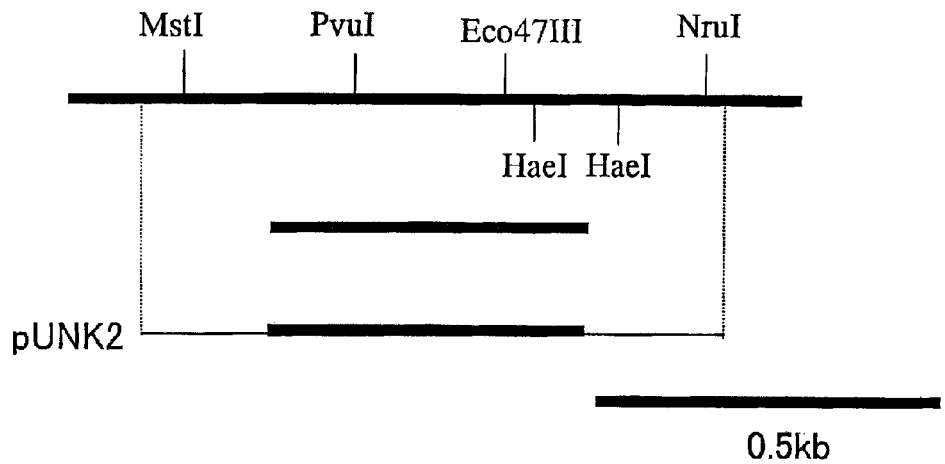

[Fig. 22]

```
MetSerGlyAlaArgGlnLysLysArgArg       10
LeuSerValTyrLeuGluProHisLeuTrp       20
LysGlyLeuArgThrGlnAlaAlaArgArg       30
SerMetSerAspSerLeuLeuAlaGluAla       40
AlaIleAlaAlaTrpLeuAspProGluGly       50
AlaGlyGlyAspProLysAlaSerLeuGlu       60
ThrAlaValGlnArgLeuAspArgArgGln       70
AlaArgIleGluArgAspLeuSerIleSer       80
ValGluThrLeuAlaLeuPheIleArgLeu       90
TrpPheThrSerMetProThrLeuSerAsp      100
SerMetAlaAlaThrAlaArgAlaGlnGly      110
AlaGluArgTyrAspArgPheValGluMet      120
LeuGlyArgArgLeuAlaSerAspLysArg      130
PheArgThrAspValAlaArgGluProAsn      140
GluGlyAspGlnThrAlaGlyGlyAlaGlu      150
```

[Fig. 23]

5'-CCCGGGGCCGGAAATGGATGTGTCGGAGGAG-3'

[Fig. 24]

5'-GGGCCCAACGTGCGTCGCGAAACGAAGAGGT-3'

[Fig. 25]

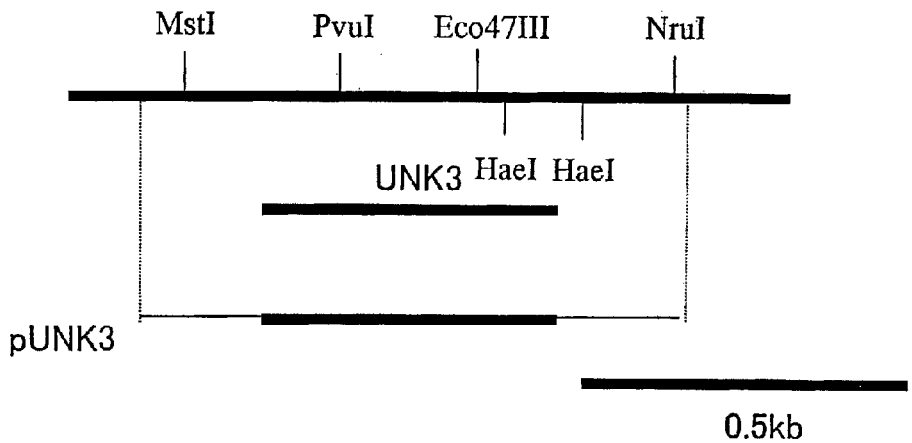

[Fig. 26]
MetGluTyrProMetSerAspLeuIleVal    10
IleGlyPheAspSerGlnAspGluAlaThr    20
AlaAlaLeuThrGluCysLysLysLeuGlu    30
LysGluTyrLeuLeuAspLeuGluAspAla    40
ValValValIleArgThrAlaAspGlyLys    50
LeuHisLeuGlnGlnSerValAsnLeuGlu    60
LysValGlyAlaSerTyrGlyLeuPheSer    70
GlyGlyPheTrpGlyAlaLeuValGlyLeu    80
LeuCysLeuAsnProLeuAlaGlyPheVal    90
AlaGlySerIleValGlyAlaGlyAlaGly   100
AlaIleAlaGlyLysMetSerAspTyrGly   110
IleAspAspAsnPheIleLysSerLeuGly   120
AlaThrIleProAlaAsnThrSerAlaLeu   130
PheIleLeuValArgLysSerGlnProAsp   140
LysValLeuAlaAspLeuArgThrPheLys   150
GlyHisAlaArgValLeuGlnThrSerLeu   160
SerProGluAsnGluAsnArgLeuArgAla   170
AlaLeuGlyGlnLeuAlaAlaProAlaThr   180
AlaAla

[Fig. 27]
5'-CCCGGGTGACACTGCGACATACGGACAACAC-3'

[Fig. 28]
5'-GGGCCCGCCCGTGCCGGGCCATGCCATGTGA-3'

[Fig. 29]
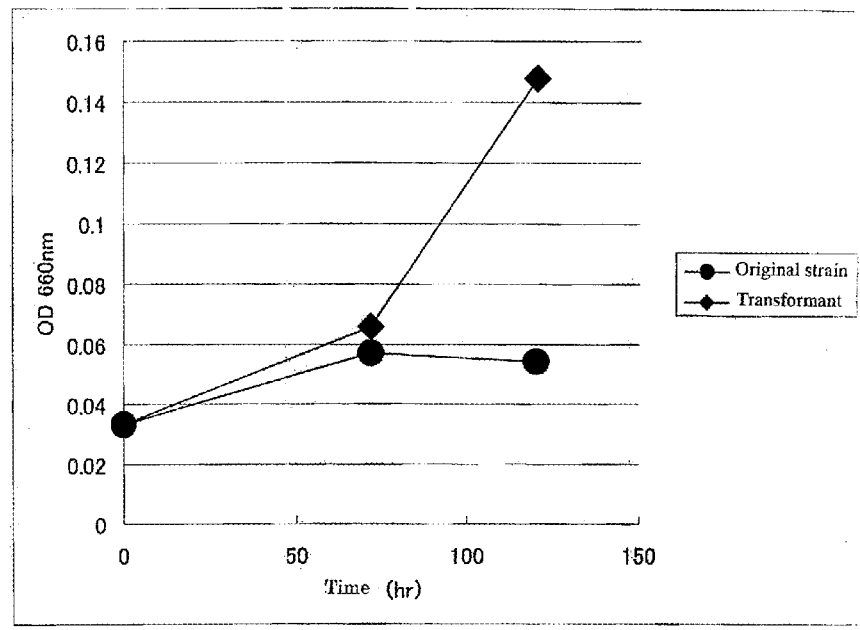
[Fig. 30]
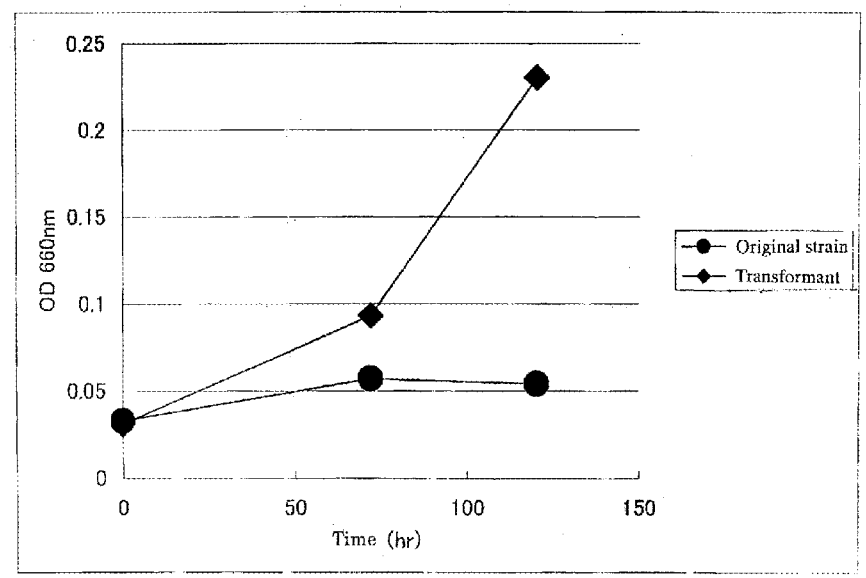

[Fig. 31]
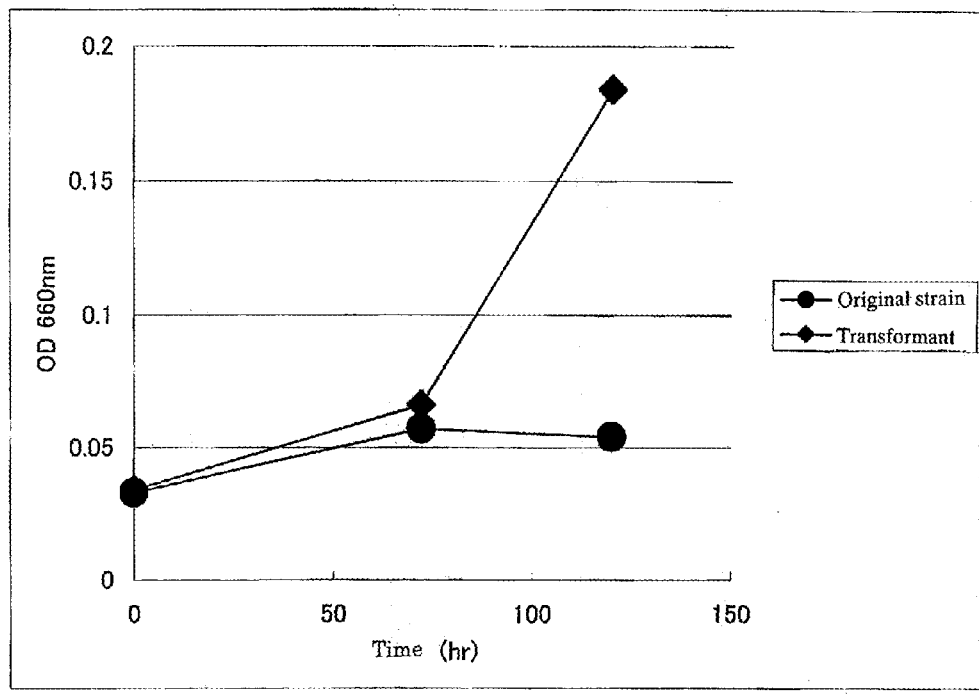
[Fig. 32]
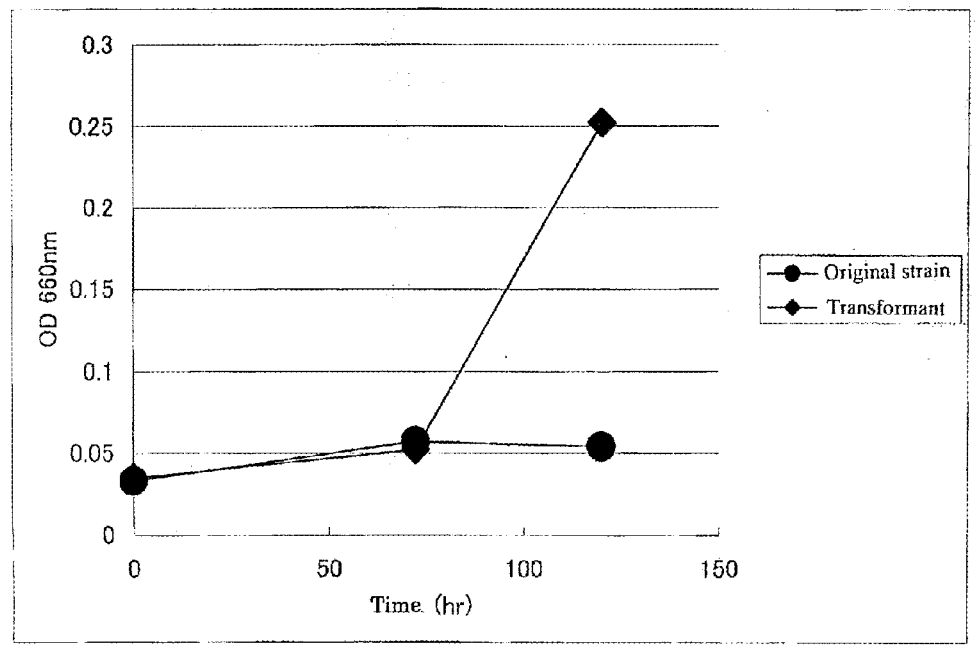

[Fig. 33]
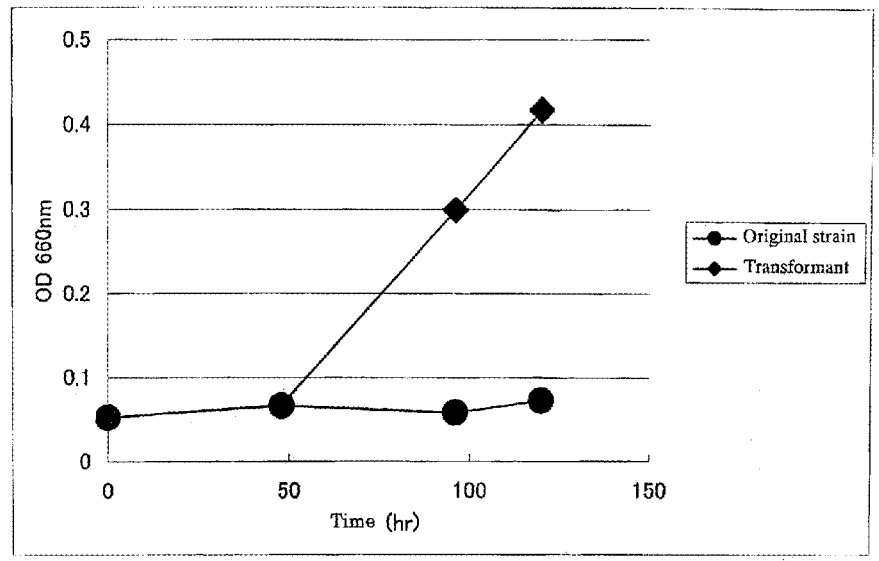
[Fig. 34]
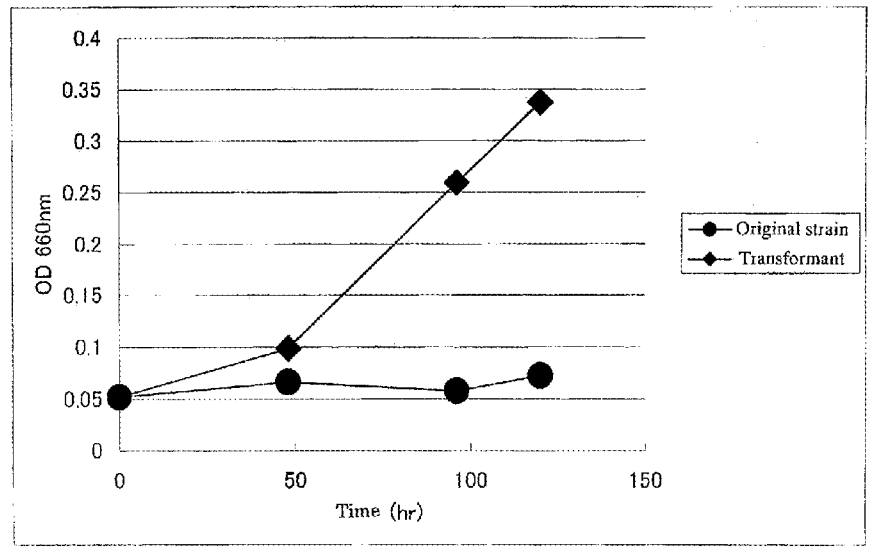

[Fig. 35]
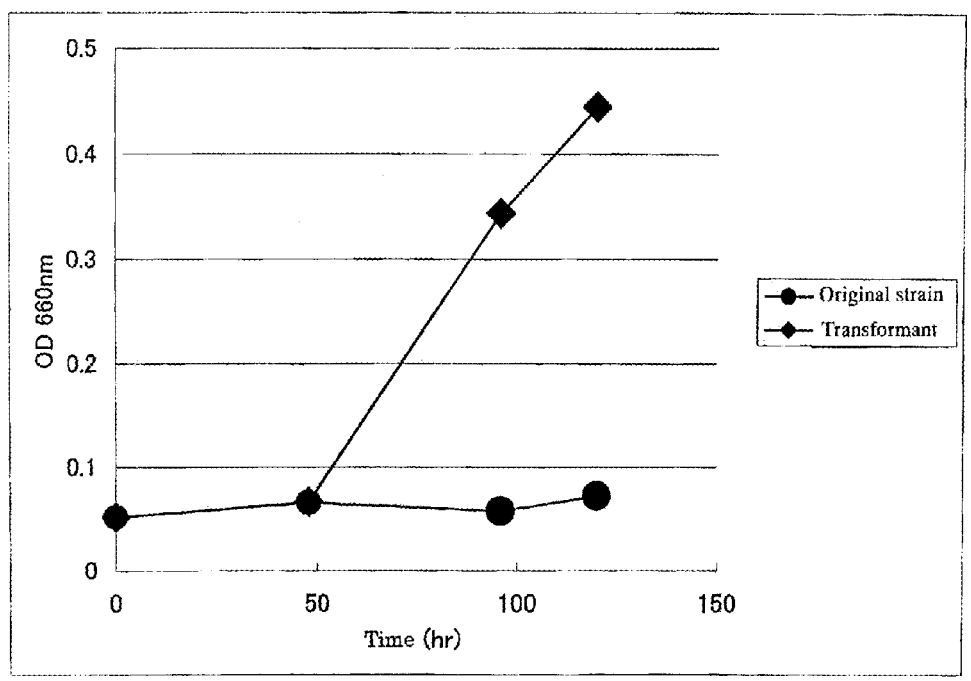

SEQUENCE LISTING

<160> NUMBER OF SEQ ID NOS: 34

<210> SEQ ID NO 1
<211> LENGTH: 960
<212> TYPE: DNA
<213> ORGANISM: Gluconacetobacter entanii(Acetobacter altoacetigenes MH-24)

<400> SEQUENCE: 1

```
cgggcggttg cggatttcga atacgagaac cagatgtttg gtatgaacca gcatatggca      60
ccggacattg acgcactgtt cctgatggcg cgggaggggc accagtacat ctcctcccgg     120
ctgatcaagg aaatcgcccg gctggatggg gacatttccg gttttgtccc gccctttacc     180
cgcaggcaca tcctcggccg cctgcgtggc tgatggaccg gggccgcctg tctggtcccg     240
ttcctcccac ccttcacttt acgaaacgga tcacgatgtc tgctacagaa aacaagtccg     300
acctgatcaa catggatctc aagacaggac gggtggtgat ccgcctgcgt cccgaccttg     360
ccccgctggc cgccgaacgc atccgtacgc tgtcggcgga agggtttat gacaacacgc     420 ccttccaccg cgtgatccac ggcttcatgg cgcagggcg tgacccgacg ggcaccggca     480
cgtcaggcag caagctgccg gacctgaagg ccgaattcac caacaaggcc aagttcgaac     540
gcggcacggt cggcatggcc cgcaccatga acccgacag cgcgaacagc cagttcttca     600
tcatgttcga accctccccg cacattgatg gccagtacac catcgtgggc caggtaatcg     660
aaggcatgga ccacattgac aaggtcaagc gtggcgcggg ccagagcggc atggtccagg     720
atcccgaccg catcatcaag atgcgcccgg ccgacgccga agcctgatta tcctgcctga     780
ccggacggcc cccacaggat gcgggctgtc cggtcagtgg ccgggatacg ggtggcccgt     840
ttcacgcggg cccctggtgt cccggcctgt tttttgcgg gccttatgcg gtcacgcaca     900
ggttgacacc cccgccgggg atgtttagag acctgcccaa ggtgtaacgc cacggtttcc     960
```

<210> SEQ ID NO 2
<211> LENGTH: 184
<212> TYPE: PRT
<213> ORGANISM: Gluconacetobacter entanii(Acetobacter altoacetigenes MH-24)

<400> SEQUENCE: 2

```
Met Asp Arg Gly Arg Leu Ser Gly Pro Val Pro Pro Thr Leu His Phe
1               5                   10                  15

Thr Lys Arg Ile Thr Met Ser Ala Thr Glu Asn Lys Ser Asp Leu Ile
            20                  25                  30

Asn Met Asp Leu Lys Thr Gly Arg Val Val Ile Arg Leu Arg Pro Asp
```

```
                  35                  40                  45
Leu Ala Pro Leu Ala Ala Glu Arg Ile Arg Thr Leu Ser Ala Glu Gly
        50                  55                  60
Phe Tyr Asp Asn Thr Pro Phe His Arg Val Ile His Gly Phe Met Ala
 65                  70                  75                  80
Gln Gly Gly Asp Pro Thr Gly Thr Gly Thr Ser Gly Ser Lys Leu Pro
                85                  90                  95
Asp Leu Lys Ala Glu Phe Thr Asn Lys Ala Lys Phe Glu Arg Gly Thr
            100                 105                 110
Val Gly Met Ala Arg Thr Met Asn Pro Asp Ser Ala Asn Ser Gln Phe
        115                 120                 125
Phe Ile Met Phe Glu Pro Ser Pro His Ile Asp Gly Gln Tyr Thr Ile
    130                 135                 140
Val Gly Gln Val Ile Glu Gly Met Asp His Ile Asp Lys Val Lys Arg
145                 150                 155                 160
Gly Ala Gly Gln Ser Gly Met Val Gln Asp Pro Asp Arg Ile Ile Lys
                165                 170                 175
Met Arg Pro Ala Asp Ala Glu Ala
            180
```

<210> SEQ ID NO 3
<211> LENGTH: 32
<212> TYPE: DNA
<213> ORGANISM: Artificial Sequence
<220> FEATURE:
<223> OTHER INFORMATION: Primer 1

<400> SEQUENCE: 3
cccgggggtt gcggatttcg aatacgagaa cc          32

<210> SEQ ID NO 4
<211> LENGTH: 31
<212> TYPE: DNA
<213> ORGANISM: Artificial Sequence
<220> FEATURE:
<223> OTHER INFORMATION: Primer 2

<400> SEQUENCE: 4
gggcccggaa accgtggcgt tacaccttgg g          31

<210> SEQ ID NO 5
<211> LENGTH: 1020
<212> TYPE: DNA
<213> ORGANISM: Gluconacetobacter entanii(Acetobacter altoacetigenes MH-24)

<400> SEQUENCE: 5
aacagggcgc agaaaaagcg gtcggggtcc gcccgacgcg catcatgcag gaacgacacg     60
cccccccgtca ccggaggaga tgcatccatc cgccccgtca tggcgtttgc tccacaaggc    120
gtggcagggg cgtgttcata tgaccgtcac ttgacgcacc cgctccacac ccatagcaat    180
cttggtatgg cggcttcatg ccgctccttg caattcccag gagaatgttc atggctttcg    240
aattgccgtc ccttcccttc gcctacaatg cccttgccaa ccgtggcatg tgccaggaaa    300
cgctggaact gcatcatgac aagcaccatc aggcctatgt gacggcactg aacggatttg    360
tcgaatccaa gcctgaactg cagggcaagt cgcttgagga atcatcctc atggtcaagg     420
gcaagcccga catggcgccc gtgttcaaca atgcgggaca gcactggaac cacatccctgt   480
tctggcagaa cctggccccc aagggcggcg agatccccca cgccctgtcc aagaagctgg   540
```

```
tcgaggattt cggcaccatt gaaaagttca aggccgattt caaggccgct gccgcatcgc    600
agttcggctc cggctgggca tggctggtgc tgggttccga tggcaagctg aaggtgacca    660
agaccgccaa cggctccaac ccgctggccg aaggccaggg caaggtactg ctgggtctgg    720
atgtgtggga gcactcctac tacctcgact tccgcaaccg tcgccccgac tacatcacca    780
actacctgga caagctggcc aactacgaat cgccgaagc gcagctgcag tccgcctgat    840
tgcctgattt caggcagtag accgaaaaac ccggccttgc gccgggtttt ttgcgtaccg    900
ggtcatgggt cgtgcctcac accccggaat gcgcccgccc gcccaacgcc cgcagcgggg    960
tgccgcgcat cagttccacc tcgatctgtt ccagcgtcat gccacgcgtc tcgggcacgc   1020
```

```
<210> SEQ ID NO 6
<211> LENGTH: 202
<212> TYPE: PRT
<213> ORGANISM: Gluconacetobacter entanii(Acetobacter altoacetigenes
      MH-24)

<400> SEQUENCE: 6

Met Ala Phe Glu Leu Pro Ser Leu Pro Phe Ala Tyr Asn Ala Leu Ala
1               5                   10                  15

Asn Arg Gly Met Cys Gln Glu Thr Leu Glu Leu His His Asp Lys His
            20                  25                  30

His Gln Ala Tyr Val Thr Ala Leu Asn Gly Phe Val Glu Ser Lys Pro
        35                  40                  45

Glu Leu Gln Gly Lys Ser Leu Glu Glu Ile Ile Leu Met Val Lys Gly
    50                  55                  60

Lys Pro Asp Met Ala Pro Val Phe Asn Asn Ala Gly Gln His Trp Asn
65                  70                  75                  80

His Ile Leu Phe Trp Gln Asn Leu Ala Pro Lys Gly Gly Glu Ile Pro
                85                  90                  95

His Ala Leu Ser Lys Lys Leu Val Glu Asp Phe Gly Thr Ile Glu Lys
            100                 105                 110

Phe Lys Ala Asp Phe Lys Ala Ala Ala Ser Gln Phe Gly Ser Gly
        115                 120                 125

Trp Ala Trp Leu Val Leu Gly Ser Asp Gly Lys Leu Lys Val Thr Lys
    130                 135                 140

Thr Ala Asn Gly Ser Asn Pro Leu Ala Glu Gly Gln Gly Lys Val Leu
145                 150                 155                 160

Leu Gly Leu Asp Val Trp Glu His Ser Tyr Tyr Leu Asp Phe Arg Asn
                165                 170                 175

Arg Arg Pro Asp Tyr Ile Thr Asn Tyr Leu Asp Lys Leu Ala Asn Tyr
            180                 185                 190

Glu Phe Ala Glu Ala Gln Leu Gln Ser Ala
        195                 200
```

```
<210> SEQ ID NO 7
<211> LENGTH: 31
<212> TYPE: DNA
<213> ORGANISM: Artificial Sequence
<220> FEATURE:
<223> OTHER INFORMATION: Primer 3

<400> SEQUENCE: 7
cccgggaaca gggcgcagaa aaagcggtcg g                                     31
```

```
<210> SEQ ID NO 8
<211> LENGTH: 31
<212> TYPE: DNA
```

<213> ORGANISM: Artificial Sequence
<220> FEATURE:
<223> OTHER INFORMATION: Primer 4

<400> SEQUENCE: 8 gggcccccccg agacgcgtgg catgacgctg g                               31

<210> SEQ ID NO 9
<211> LENGTH: 780
<212> TYPE: DNA
<213> ORGANISM: Gluconacetobacter entanii(Acetobacter altoacetigenes MH-24)

<400> SEQUENCE: 9
cgcagggctg acccgcccgc gcccattcga tcaggagatc cagggatcc cgcgtggatg      60
aaacctgtgt catagcagga ctactctatc agcacgcata cactcatgcc agccggtgga    120
catgtacgaa caggcatccc atatattgcc acaacataac gccaccccga tgtggggcgc    180
gcatgaatgg agtactgtaa atgagttatg tcgatcctgc ctggtatgtt gttgccgata    240
acattcatgc ccgcatcctg aagcatggcg aacatggtct tgcgacgttc gagcacctca    300
agagcgacga tgcaaagggc atggatgctc gcgtaacgg tgcctatggc aaggtcattg      360
cggaattcct gaacacggtc gtgcgccaga agaaggctcc ggccatcgcg atcgcggccc    420
ccggtgatgt catgcaccag atccgcgcgc atctggacgt gcacaccgt gcgctggtgg      480
tcaaggaact ggagcgtgac ctgaccaaca ccccgatca tgaactggcc aagcatttcg     540
acattccggc caccggctgg ccgctgccca acgcgggctg atcggctact ggtcgcctgt    600
tgcgccccgc ggtaacgtgg ggcgcttttt tatatgtagg gttccccgca tgccgacacc    660
tctttccctt gaaatcgtgc ccgtcaccgc ctttggccag aactgttcca tattatggaa    720
tcccgacacg catcatgccg tcgtggtcga tccggggggt gatgtgccgc gtatcatggc    780

<210> SEQ ID NO 10
<211> LENGTH: 126
<212> TYPE: PRT
<213> ORGANISM: Gluconacetobacter entanii(Acetobacter altoacetigenes MH-24)

<400> SEQUENCE: 10

Met Ser Tyr Val Asp Pro Ala Trp Tyr Val Ala Asp Asn Ile His
1               5                   10                  15

Ala Arg Ile Leu Lys His Gly Glu His Gly Leu Ala Thr Phe Glu His
            20                  25                  30

Leu Lys Ser Asp Asp Ala Lys Gly Met Asp Ala Pro Arg Asn Gly Ala
        35                  40                  45

Tyr Gly Lys Val Ile Ala Glu Phe Leu Asn Thr Val Val Arg Gln Lys
    50                  55                  60

Lys Ala Pro Ala Ile Ala Ile Ala Ala Pro Gly Asp Val Met His Gln
65                  70                  75                  80

Ile Arg Ala His Leu Asp Val His Thr Arg Ala Leu Val Val Lys Glu
                85                  90                  95

Leu Glu Arg Asp Leu Thr Asn Thr Pro Asp His Glu Leu Ala Lys His
            100                 105                 110

Phe Asp Ile Pro Ala Thr Gly Trp Pro Leu Pro Asn Ala Gly
        115                 120                 125

<210> SEQ ID NO 11
<211> LENGTH: 31
<212> TYPE: DNA

<213> ORGANISM: Artificial Sequence
<220> FEATURE:
<223> OTHER INFORMATION: Primer 5

<400> SEQUENCE: 11
cccgggggcc tgctggaccg cgtgcgcttc c                                    31

<210> SEQ ID NO 12
<211> LENGTH: 31
<212> TYPE: DNA
<213> ORGANISM: Artificial Sequence
<220> FEATURE:
<223> OTHER INFORMATION: Primer 6

<400> SEQUENCE: 12 gggcccccgga aaccggaggc atgggcaccg c                                   31

<210> SEQ ID NO 13
<211> LENGTH: 960
<212> TYPE: DNA
<213> ORGANISM: Gluconacetobacter entanii(Acetobacter altoacetigenes MH-24)

<400> SEQUENCE: 13
caggtgctgg aatcggtcga ggaaaaggac cgtaacgaaa cctatcagcg caagacgctg      60
atgatccagc gtatcgaggc cctggcccgc gccgccgccg aaagcaagaa cggggatcag     120
gtcatcaccc tgacatcgga agaattctgg ctgatcagcc agaactggta atcttccccc     180
aaccggccaa cgttgacccc tatccgcgcg gcctgtcgcg cggaaagcag gaaaccgaca     240
tgacgtttac actgacaagc cgctccttcc acgatggcga ccgcctgccc gcggcgcagg     300
tgtttgacgg gatgggttat tcaggcggca acatctcgcc gccgctggca tgcaggatc      360
cgcccgctgg caccaagagc ttcgccatca ccatgtatga tcccgacgcc ccgacgggtt     420
cgggctggtg gcactgggtt gtcatcaaca tccccgccac ggtgtcatcc ctgcctgcgg     480
gcgcgggatc gggcgacaac gacctgcctg aacacgccga gatgacgcgc accgatttcg     540
gcgggaatgt ctatggcggc gcagcacccc cgccgggacc ggaccaccat tacattttca     600
ccatccatgc gctggacatc gaacggatcg aactgcccaa cgatgcatcg gcgccatgg      660
tgggctttgt catcaaccag cacagccttg gttccgccaa gctgaccgcc gtatttggca     720
agcagccgaa ataacaccgc cctgctgccg cgcatgcgtg cgcggcagca ataaataact     780
gataaataat aaaagttccc gaatgccgcg ttatccctga taggacgcga tttcgatcag     840
gttgccatcg gggtcatgac aatagaccga tgtaaccggc cccagcgccc ccagacgggc     900
taccggtccc tccgttaccc ggacaccgca ttttcaagg tgttcaatga catcgacact     960

<210> SEQ ID NO 14
<211> LENGTH: 164
<212> TYPE: PRT
<213> ORGANISM: Gluconacetobacter entanii(Acetobacter altoacetigenes MH-24)

<400> SEQUENCE: 14

Met Thr Phe Thr Leu Thr Ser Arg Ser Phe His Asp Gly Asp Arg Leu
1               5                   10                  15

Pro Ala Ala Gln Val Phe Asp Gly Met Gly Tyr Ser Gly Gly Asn Ile
            20                  25                  30

Ser Pro Pro Leu Ala Trp Gln Asp Pro Ala Gly Thr Lys Ser Phe
        35                  40                  45

Ala Ile Thr Met Tyr Asp Pro Asp Ala Pro Thr Gly Ser Gly Trp Trp

```
            50                 55                  60
His Trp Val Val Ile Asn Ile Pro Ala Thr Val Ser Ser Leu Pro Ala
 65                  70                  75                  80

Gly Ala Gly Ser Gly Asp Asn Asp Leu Pro Glu His Ala Glu Met Thr
                 85                  90                  95

Arg Thr Asp Phe Gly Gly Asn Val Tyr Gly Ala Ala Pro Pro Pro Pro
            100                 105                 110

Gly Pro Asp His His Tyr Ile Phe Thr Ile His Ala Leu Asp Ile Glu
            115                 120                 125

Arg Ile Glu Leu Pro Asn Asp Ala Ser Gly Ala Met Val Gly Phe Val
130                 135                 140

Ile Asn Gln His Ser Leu Gly Ser Ala Lys Leu Thr Ala Val Phe Gly
145                 150                 155                 160

Lys Gln Pro Lys

<210> SEQ ID NO 15
<211> LENGTH: 32
<212> TYPE: DNA
<213> ORGANISM: Artificial Sequence
<220> FEATURE:
<223> OTHER INFORMATION: Primer 7

<400> SEQUENCE: 15 cccggggtg ctggaatcgg tcgaggaaaa gg                                32

<210> SEQ ID NO 16
<211> LENGTH: 31
<212> TYPE: DNA
<213> ORGANISM: Artificial Sequence
<220> FEATURE:
<223> OTHER INFORMATION: Primer 8

<400> SEQUENCE: 16
gggcccggtg tccgggtaac ggagggaccg g                                31

<210> SEQ ID NO 17
<211> LENGTH: 960
<212> TYPE: DNA
<213> ORGANISM: Gluconacetobacter entanii(Acetobacter altoacetigenes
       MH-24)

<400> SEQUENCE: 17
gccaccacat attcgatgtc gcgcagcgac aggcccgaaa gaggaatata attcatatct    60
atagatagga ccgatttcgt ggcatttgta aaaaggtttt tccgatcaga cccattgaca   120
gaaacggttt ctccccattt cgtgtttgtg ggacagatac ccggtcaata actgacaagc   180
caaagcaagg agcattccgc atggcacgca tcaattcgtc tctgaagccg ttcgagacag   240
acgccttcca caacggaaag ttcatcaagg tgagcgatgc cgacgtgaag ggcaaatggt   300
ccgtcttctt cttctatccg gcggatttca ccttcgtctg cccgacggaa ctggaagacc   360
tggctgaaaa ttacgagacg ttccagaagt tgggcgtgga aatctactcg gtttcgaccg   420
acaagcattt cacccacaag gcatggcacg acacgtcacc ggccatcagc aagatcaagt   480
tcgtgatgct gggcgacccg accgcccaca tcgcacgtaa ttttgatgtc tatatcgagg   540
aagcgggcgt ggccgaccgc ggcaccttcc tgatcgatcc ggaaggcagg atccagtaca   600
tcgaaattac cgctggcagc gtcggccgca gcgccgccga actgatcgcc aagatcgagg   660
ccgcgcagta cgtcgcgtcc caccccggcg aagtctgccc ggcgaagtgg aaggaaggcg   720
gtgccacgct gaccccgtcg ctggacctcg tcggcaagat ctgacgccca tggccccggc   780
```

```
ccggtcctgc aggaccgggc cacccatgcc accttttccc aaagagcgga gtccattccc      840
atgttgcaag atcccatcaa gacgcagctc aagggttatc tggccagcct tgcgcacccg      900
atcgtgctgg aggccagcct ggatgacacc tccgcttcgc gtgagatgca tgaactcctg      960
```

<210> SEQ ID NO 18
<211> LENGTH: 187
<212> TYPE: PRT
<213> ORGANISM: Gluconacetobacter entanii(Acetobacter altoacetigenes MH-24)

<400> SEQUENCE: 18

```
Met Ala Arg Ile Asn Ser Ser Leu Lys Pro Phe Glu Thr Asp Ala Phe
1               5                   10                  15

His Asn Gly Lys Phe Ile Lys Val Ser Asp Ala Asp Val Lys Gly Lys
            20                  25                  30

Trp Ser Val Phe Phe Tyr Pro Ala Asp Phe Thr Phe Val Cys Pro
        35                  40                  45

Thr Glu Leu Glu Asp Leu Ala Glu Asn Tyr Glu Thr Phe Gln Lys Leu
    50                  55                  60

Gly Val Glu Ile Tyr Ser Val Ser Thr Asp Lys His Phe Thr His Lys
65                  70                  75                  80

Ala Trp His Asp Thr Ser Pro Ala Ile Ser Lys Ile Lys Phe Val Met
                85                  90                  95

Leu Gly Asp Pro Thr Ala His Ile Ala Arg Asn Phe Asp Val Tyr Ile
            100                 105                 110

Glu Glu Ala Gly Val Ala Asp Arg Gly Thr Phe Leu Ile Asp Pro Glu
        115                 120                 125

Gly Arg Ile Gln Tyr Ile Glu Ile Thr Ala Gly Ser Val Gly Arg Ser
    130                 135                 140

Ala Ala Glu Leu Ile Ala Lys Ile Glu Ala Ala Gln Tyr Val Ala Ser
145                 150                 155                 160

His Pro Gly Glu Val Cys Pro Ala Lys Trp Lys Glu Gly Gly Ala Thr
                165                 170                 175

Leu Thr Pro Ser Leu Asp Leu Val Gly Lys Ile
            180                 185
```

<210> SEQ ID NO 19
<211> LENGTH: 31
<212> TYPE: DNA
<213> ORGANISM: Artificial Sequence
<220> FEATURE:
<223> OTHER INFORMATION: Primer 9

<400> SEQUENCE: 19

```
cccggggcca ccacatattc gatgtcgcgc a                                     31
```

<210> SEQ ID NO 20
<211> LENGTH: 31
<212> TYPE: DNA
<213> ORGANISM: Artificial Sequence
<220> FEATURE:
<223> OTHER INFORMATION: Primer 10

<400> SEQUENCE: 20

```
gggcccccagg agttcatgca tctcacgcga a                                    31
```

<210> SEQ ID NO 21
<211> LENGTH: 840
<212> TYPE: DNA

<213> ORGANISM: Gluconacetobacter entanii(Acetobacter altoacetigenes MH-24)

<400> SEQUENCE: 21

```
gccggaaatg gatgtgtcgg aggagcccga cctaccgcag caggatgaca gcgatccctc    60
gcatgaagtt tccatgcgca agcgtgaacg cgatccgatg gaagaggaag atctccatgc   120
cgtgctgacg gcggacctcg cccgcaaagc acgtcaggcc gccctcgatc ctggcaatga   180
tctggggatg tcatgagcgg agcgcgccag aagaagaggc ggctttcggt ctatctggag   240
ccgcatctgt ggaaggggct acggacgcag gccgcccgac ggtcgatgtc ggactctctg   300
ctggccgaag ccgcgatcgc cgcctggctt gacccggaag gcgcgggtgg tgaccccaaa   360
gcgtcgctcg aaaccgccgt gcaacgactt gatcgccgac aggcgcggat cgaacgtgac   420
ctgtcgatct cggttgagac cctcgcactg ttcatccggc tctggttcac cagtatgccg   480
actctctcag acagcatggc ggccacggcg cgtgcccagg gggcggagcg ctacgaccgg   540
ttcgtcgaga tgctgggcag agactggcc agcgacaagg ggttccggac agatgtcgca   600
cgcgagccaa acgagggtga ccagactgcg ggcggggcgg agtgaggaac cacgtccgaa   660
acgcccggtc agatcagcga gagaatgcgt tggccagccg atgttcatcc ccctttctgg   720
ccgacgactc ttttctcccg gtcctggctg catttcgcgt ggaaggcggc tgtttctccc   780
cggacagggg aacaggcgca atggtttcct ccccgacctc ttcgtttcgc gacgcacgtt   840
```

<210> SEQ ID NO 22
<211> LENGTH: 150
<212> TYPE: PRT
<213> ORGANISM: Gluconacetobacter entanii(Acetobacter altoacetigenes MH-24)

<400> SEQUENCE: 22

```
Met Ser Gly Ala Arg Gln Lys Lys Arg Arg Leu Ser Val Tyr Leu Glu
1               5                   10                  15

Pro His Leu Trp Lys Gly Leu Arg Thr Gln Ala Ala Arg Arg Ser Met
            20                  25                  30

Ser Asp Ser Leu Leu Ala Glu Ala Ala Ile Ala Ala Trp Leu Asp Pro
        35                  40                  45

Glu Gly Ala Gly Gly Asp Pro Lys Ala Ser Leu Glu Thr Ala Val Gln
    50                  55                  60

Arg Leu Asp Arg Arg Gln Ala Arg Ile Glu Arg Asp Leu Ser Ile Ser
65                  70                  75                  80

Val Glu Thr Leu Ala Leu Phe Ile Arg Leu Trp Phe Thr Ser Met Pro
                85                  90                  95

Thr Leu Ser Asp Ser Met Ala Ala Thr Ala Arg Ala Gln Gly Ala Glu
            100                 105                 110

Arg Tyr Asp Arg Phe Val Glu Met Leu Gly Arg Arg Leu Ala Ser Asp
        115                 120                 125

Lys Arg Phe Arg Thr Asp Val Ala Arg Glu Pro Asn Glu Gly Asp Gln
    130                 135                 140

Thr Ala Gly Gly Ala Glu
145                 150
```

<210> SEQ ID NO 23
<211> LENGTH: 31
<212> TYPE: DNA
<213> ORGANISM: Artificial Sequence
<220> FEATURE:
<223> OTHER INFORMATION: Primer 11

-continued

<400> SEQUENCE: 23 cccgggccg gaaatggatg tgtcggagga g                               31

<210> SEQ ID NO 24
<211> LENGTH: 31
<212> TYPE: DNA
<213> ORGANISM: Artificial Sequence
<220> FEATURE:
<223> OTHER INFORMATION: Primer 12

<400> SEQUENCE: 24
gggcccaacg tgcgtcgcga aacgaagagg t                              31

<210> SEQ ID NO 25
<211> LENGTH: 960
<212> TYPE: DNA
<213> ORGANISM: Gluconacetobacter entanii(Acetobacter altoacetigenes
    MH-24)

<400> SEQUENCE: 25
tgacactgcg acatacggac aaacacatatg acaggggggac ggttcgccac catgtccgtc     60
atgagccgct tcatggcaga tgggatatcc ggcctgcgcc cgcaaccggg ccagacctgc    120
accccaccgg gggcatccat gcctaaaaac cgccacggca tgaaggatat atccatgtaa    180
tatcatggtg accatccgcc cccaccatcc ggggcggag acatgcaatg gagtatccca    240
tgtccgatct gatcgttatc ggttttgaca gccaggacga agccacggct gccctgaccg    300
aatgcaagaa gctggaaaag gaatacctgc tggacctgga ggacgcggtt gtcgtcatcc    360
gcaccgccga tggcaagctg cacctgcagc agagcgtcaa cctggaaaag gtcggcgcgt    420
cgtatggcct gttctctggc gggttctggg gcgcgctggt tggcctgctg tgcctgaacc    480
cgctggcggg ttttgtcgcg ggcagcatcg tgggtgccgg tgcgggcgcg atcgcgggca    540
agatgtccga ctacggcatt gatgacaatt tcatcaagtc gctgggcgcc accatcccgg    600
ccaacacgtc cgcgctgttc attctggtgc gcaagtccca gcccgacaag gttctggccg    660
acctgcgcac gttcaagggc catgcccgcg tgctgcagac ctcgcttcct ccggaaaacg    720
aaaacaggct gcgcgcggcc ctgggccagc tggcggcccc cgccacggcg gcctgaatgc    780
ctgtcccaca tgccgcccgt ggcatgtggg accttgccca cacacaggcg tgatgaccga    840
tcaccccgcg taatgatatg ctgggcatat gccgaccacc cgtcagcgcc tgcgccgcgt    900
gttcctgtca ttttttctgg ccattccggc cgctgtcaca tggcatggcc cggcacgggc    960

<210> SEQ ID NO 26
<211> LENGTH: 182
<212> TYPE: PRT
<213> ORGANISM: Gluconacetobacter entanii(Acetobacter altoacetigenes
    MH-24)

<400> SEQUENCE: 26

Met Glu Tyr Pro Met Ser Asp Leu Ile Val Ile Gly Phe Asp Ser Gln
1               5                   10                  15

Asp Glu Ala Thr Ala Ala Leu Thr Glu Cys Lys Lys Leu Glu Lys Glu
            20                  25                  30

Tyr Leu Leu Asp Leu Glu Asp Ala Val Val Val Ile Arg Thr Ala Asp
        35                  40                  45

Gly Lys Leu His Leu Gln Gln Ser Val Asn Leu Glu Lys Val Gly Ala
    50                  55                  60

Ser Tyr Gly Leu Phe Ser Gly Gly Phe Trp Gly Ala Leu Val Gly Leu
65                  70                  75                  80

```
Leu Cys Leu Asn Pro Leu Ala Gly Phe Val Ala Gly Ser Ile Val Gly
                 85                  90                  95

Ala Gly Ala Gly Ala Ile Ala Gly Lys Met Ser Asp Tyr Gly Ile Asp
            100                 105                 110

Asp Asn Phe Ile Lys Ser Leu Gly Ala Thr Ile Pro Ala Asn Thr Ser
            115                 120                 125

Ala Leu Phe Ile Leu Val Arg Lys Ser Gln Pro Asp Lys Val Leu Ala
    130                 135                 140

Asp Leu Arg Thr Phe Lys Gly His Ala Arg Val Leu Gln Thr Ser Leu
145                 150                 155                 160

Ser Pro Glu Asn Glu Asn Arg Leu Arg Ala Ala Leu Gly Gln Leu Ala
                165                 170                 175

Ala Pro Ala Thr Ala Ala
            180
```

<210> SEQ ID NO 27
<211> LENGTH: 31
<212> TYPE: DNA
<213> ORGANISM: Artificial Sequence
<220> FEATURE:
<223> OTHER INFORMATION: Primer 13

<400> SEQUENCE: 27
cccgggtgac actgcgacat acggacaaca c        31

<210> SEQ ID NO 28
<211> LENGTH: 31
<212> TYPE: DNA
<213> ORGANISM: Artificial Sequence
<220> FEATURE:
<223> OTHER INFORMATION: Primer 14

<400> SEQUENCE: 28
gggcccgccc gtgccgggcc atgccatgtg a        31

<210> SEQ ID NO 29
<211> LENGTH: 10
<212> TYPE: PRT
<213> ORGANISM: Gluconacetobacter entanii(Acetobacter altoacetigenes
      MH-24)

<400> SEQUENCE: 29

```
Met Asp Gln Glu Ser Lys Arg Arg Ala Thr
1               5                   10
```

<210> SEQ ID NO 30
<211> LENGTH: 10
<212> TYPE: PRT
<213> ORGANISM: Gluconacetobacter entanii(Acetobacter altoacetigenes
      MH-24)

<400> SEQUENCE: 30

```
Met Arg Ser Ile Arg Ile Met Ala Gln Ile
1               5                   10
```

<210> SEQ ID NO 31
<211> LENGTH: 10
<212> TYPE: PRT
<213> ORGANISM: Gluconacetobacter entanii(Acetobacter altoacetigenes
      MH-24)

<400> SEQUENCE: 31

Met Ser Arg His Arg Ala Arg Arg Lys Gly

```
<210> SEQ ID NO 32
<211> LENGTH: 30
<212> TYPE: DNA
<213> ORGANISM: Artificial Sequence
<220> FEATURE:
<223> OTHER INFORMATION: AAR8 Probe

<400> SEQUENCE: 32
gtggatcagg aatcaaaaag gagggccaca                              30

<210> SEQ ID NO 33
<211> LENGTH: 30
<212> TYPE: DNA
<213> ORGANISM: Artificial Sequence
<220> FEATURE:
<223> OTHER INFORMATION: AAR9 Probe

<400> SEQUENCE: 33
gtgaggagta tcaggataat ggcgcagatt                              30

<210> SEQ ID NO 34
<211> LENGTH: 30
<212> TYPE: DNA
<213> ORGANISM: Artificial Sequence
<220> FEATURE:
<223> OTHER INFORMATION: AAR10 Probe

<400> SEQUENCE: 34
atgtctcgac atcgtgcgag gaggaagggt                              30
```

GENE RELATED TO GROWTH PROMOTING FUNCTION OF ACETIC ACID BACTERIUM, ACETIC ACID BACTERIUM BRED USING THE GENE AND METHOD FOR PRODUCING VINEGAR USING THE ACETIC ACID BACTERIUM

TECHNICAL FIELD

The present invention relates to a gene that encodes a protein derived from microorganisms and having a function of promoting growth in the presence of acetic acid; microorganisms with amplified copies of the gene, particularly, acetic acid bacteria belonging to the genus *Acetobacter* and the genus *Gluconacetobacter*; and a method for efficiently producing vinegar containing a high concentration of acetic acid in a short time using these microorganisms.

BACKGROUND ART

Acetic acid bacteria are microorganisms widely utilized for producing vinegar. Particularly, acetic acid bacteria belonging to the genus *Acetobacter* or the genus *Gluconacetobacter* are utilized in industrial acetic acid fermentation.

In acetic acid fermentation, ethanol in a medium is oxidized and converted to acetic acid by acetic acid bacteria. As a result, acetic acid accumulates in the medium. Acetic acid is also inhibitory on acetic acid bacteria, and the growth ability and the fermentation ability of acetic acid bacteria gradually decrease as the amount of accumulated acetic acid increases and the concentration of acetic acid in the medium becomes higher.

For example, it has been observed that the period from the initiation of fermentation to the time when acetic acid bacteria actually start growing and the accumulation of acetic acid can be confirmed, i.e., the period referred to as growth induction period, tends to be longer as the concentration of acetic acid becomes higher. It has been also confirmed that the growth rate and the growth amount of acetic acid bacteria decrease as the concentration of acetic acid becomes higher.

In order to improve by breeding the above-mentioned growth ability of acetic acid bacteria in the presence of acetic acid, an effort has been made for obtaining a gene that encodes a protein having a function of promoting acetic acid bacterial growth in the presence of acetic acid and enhancing the acetic acid bacteria's function of promoting growth, thereby developing acetic acid bacteria with an improved fermentation ability in a high concentration of acetic acid. For example, the ompA gene of acetic acid bacteria, which is highly homologous to the ompA gene of *Escherichia coli* and the like, was cloned and the gene was confirmed to have a function of promoting acetic acid bacterial growth in the presence of acetic acid (for example, see patent document 1), but the effect was less than sufficient.

Further, based on the assumption that there exists a protein involved in the adaptative mechanism to a high concentration of acetic acid, in a group of proteins expressed in acetic acid bacteria being cultured in a high concentration of acetic acid, it has been reported that there are some proteins in the above protein group that are highly homologous to protease I, pectate lyase II precursor, ubiquinone oxidoreductase, chaperon GroEL and the like in terms of N-terminal-side amino acid sequences (for example, see non-patent document 1). It has, however, not been confirmed whether these proteins have a function of promoting acetic acid bacterial growth in the presence of acetic acid.

For the above reasons, it has been awaited to obtain a gene that encodes a protein having a function of promoting growth in the presence of acetic acid and to enhance the acetic acid bacteria's function of promoting growth in the presence of acetic acid by using the gene, thereby to develop acetic acid bacteria with an improved fermentation ability in a high concentration of acetic acid.

Patent Document 1: International Publication No. WO2005/001095

Non-Patent Document 1: Appl. Environ. Microbiol. Vol. 67, pp. 5474-5481, 2001

DISCLOSURE OF THE INVENTION

Object to be Solved by the Invention

The object to be solved by the present invention is to obtain a novel gene that encodes a protein having a function of promoting acetic acid bacterial growth in the presence of a high concentration of acetic acid; to enhance the acetic acid bacteria's function of promoting growth, thereby to develop acetic acid bacteria with an improved fermentation ability in a high concentration of acetic acid; and to provide a method for efficiently producing vinegar containing a high concentration of acetic acid in a short time by using the acetic acid bacteria.

Means to Solve the Object

The present inventor made an assumption that, in acetic acid bacteria capable of growing and fermenting even in the presence of acetic acid, there exists a specific protein that does not exist in other microorganisms and that has a tolerance for acetic acid. The present inventor obtained a novel concept that, by using a gene that encodes such protein, the microorganism's function of promoting growth in the presence of acetic acid can be improved than before, and further that this would allow the development of a method for efficiently producing novel vinegar containing acetic acid in a concentration as high as that could not have been obtained in the past.

Consequently, as a result of a keen study on a method for finding from acetic acid bacteria a gene having a function of promoting growth in the presence of acetic acid, the present inventor has reached the idea that a protein having a function of promoting growth in the presence of acetic acid can be detected by exposing acetic acid bacterial proteins to a high concentration of acetic acid and then searching for a protein that has not been denatured but still exists as a soluble protein. Thus, acetic acid adjusted to pH 4.0 was added to an acetic acid bacterial lysate to a final concentration of 1 M, and proteins that were insoluble in the presence of acetic acid were removed centrifugally. Then soluble proteins were separated by two-dimensional electrophoresis and the N-terminal amino acid sequence of the protein was identified. Thereafter, using the DNA prepared from the identified N-terminal amino acid sequence as a probe, a colony hybridization was performed to identify a gene, thereby a gene that encodes a protein capable of promoting growth in the presence of acetic acid was isolated. Further, the identified gene was transformed into *Acetobacter aceti* No. 1023 strain (deposited under Accession Number: FERM BP-2287 on Feb. 13, 1989 with the International Patent Organism Depositary (IPOD) AIST (Address: Tsukuba Central 6, 1-1, Higashi 1-Chome, Tsukuba-shi, Ibaraki-Ken, 305-8566 Japan)) to confirm that the transformant advantageously promotes growth as compared to the original strain, and thus the present invention was completed.

More specifically, the present invention relates to: ("1") a protein of following (A), (B) or (C): (A) a protein consisting of the amino acid sequence shown in SEQ ID NO: 2 in the sequence listing, (B) a protein consisting of an amino acid sequence comprising a substitution, deletion, insertion, addition, or inversion of one or several amino acids in the amino acid sequence shown in SEQ ID NO: 2 in the sequence listing, which protein has a function of promoting growth in the presence of acetic acid, (C) a protein consisting of an amino acid sequence having at least 85% or more homology to the amino acid sequence shown in SEQ ID NO: 2 in the sequence listing, which protein has a function of promoting growth in the presence of acetic acid; ("2") a DNA that encodes a protein shown in the following (A), (B), or (C): (A) a protein consisting of the amino acid sequence shown in SEQ ID NO: 2 in the sequence listing, (B) a protein consisting of an amino acid sequence comprising a substitution, deletion, insertion, addition, or inversion of one or several amino acids in the amino acid sequence shown in SEQ ID NO: 2 in the sequence listing, which protein has a function of promoting growth in the presence of acetic acid, (C) a protein consisting of an amino acid sequence having at least 85% or more homology to the amino acid sequence shown in SEQ ID NO: 2 in the sequence listing, which protein has a function of promoting growth in the presence of acetic acid; and ("3") a DNA of following (A), (B), (C) or (D): (A) a DNA consisting of the nucleotide sequence (base sequence) of nucleotide numbers 213 to 764 of the nucleotide sequence shown in SEQ ID NO: 1 in the sequence listing, (B) a DNA that hybridizes under stringent conditions with a DNA consisting of a sequence complementary to the nucleotide sequence of nucleotide numbers 213 to 764 in the nucleotide sequence shown in SEQ ID NO: 1 in the sequence listing, which DNA encodes a protein having a function of promoting growth in the presence of acetic acid, (C) a DNA that hybridizes under stringent conditions with a DNA consisting of a nucleotide sequence having a function as a primer or a probe that is produced from a part of the nucleotide sequence of nucleotide numbers 213 to 764 in the nucleotide sequence shown in SEQ ID NO: 1 in the sequence listing, which DNA encodes a protein having a function of promoting growth in the presence of acetic acid, (D) a DNA consisting of a nucleotide sequence comprising a substitution, deletion, insertion, addition, or inversion of one or several nucleotides in the nucleotide sequence of nucleotide numbers 213 to 764 in the nucleotide sequence shown in SEQ ID NO: 1 in the sequence listing, which DNA encodes a protein having a function of promoting growth in the presence of acetic acid.

Further, the present invention relates to: ("4") a protein of following (A), (B), or (C): (A) a protein consisting of the amino acid sequence shown in SEQ ID NO: 6 in the sequence listing, (B) a protein consisting of an amino acid sequence comprising a substitution, deletion, insertion, addition, or inversion of one or several amino acids in the amino acid sequence shown in SEQ ID NO: 6 in the sequence listing, which protein has a function of promoting growth in the presence of acetic acid, (C) a protein consisting of an amino acid sequence having at least 85% or more homology to the amino acid sequence shown in SEQ ID NO: 6 in the sequence listing, which protein has a function of promoting growth in the presence of acetic acid; ("5") a DNA that encodes a protein shown in following (A), (B), or (C): (A) a protein consisting of the amino acid sequence shown in SEQ ID NO: 6 in the sequence listing, (B) a protein consisting of an amino acid sequence comprising a substitution, deletion, insertion, addition, or inversion of one or several amino acids in the amino acid sequence shown in SEQ ID NO: 6 in the sequence listing, which protein has a function of promoting growth in the presence of acetic acid, (C) a protein consisting of an amino acid sequence having at least 85% or more homology to the amino acid sequence shown in SEQ ID NO: 6 in the sequence listing, which protein has a function of promoting growth in the presence of acetic acid; and ("6") a DNA of following (A), (B), (C), or (D): (A) a DNA consisting of the nucleotide sequence of nucleotide numbers 231 to 836 in the nucleotide sequence shown in SEQ ID NO: 5 in the sequence listing, (B) a DNA that hybridizes under stringent conditions with a DNA consisting of a sequence complementary to the nucleotide sequence of nucleotide numbers 231 to 836 in the nucleotide sequence shown in SEQ ID NO: 5 in the sequence listing, which DNA encodes a protein having a function of promoting growth in the presence of acetic acid, (C) a DNA that hybridizes under stringent conditions with a DNA consisting of a nucleotide sequence having a function as a primer or a probe that is produced from a part of the nucleotide sequence of nucleotide numbers 231 to 836 in the nucleotide sequence shown in SEQ ID NO: 5 in the sequence listing, which DNA encodes a protein having a function of promoting growth in the presence of acetic acid, (D) a DNA consisting of a nucleotide sequence comprising a substitution, deletion, insertion, addition, or inversion of one or several nucleotides in the nucleotide sequence of nucleotide numbers 231 to 836 in the nucleotide sequence shown in SEQ ID NO: 5 in the sequence listing, which DNA encodes a protein having a function of promoting growth in the presence of acetic acid.

Further, the present invention relates to: ("7") a protein of following (A), (B), or (C): (A) a protein consisting of the amino acid sequence shown in SEQ ID NO: 10 in the sequence listing, (B) a protein consisting of an amino acid sequence comprising a substitution, deletion, insertion, addition, or inversion of one or several amino acids in the amino acid sequence shown in SEQ ID NO: 10 in the sequence listing, which protein has a function of promoting growth in the presence of acetic acid, (C) a protein consisting of an amino acid sequence having at least 85% or more homology to the amino acid sequence shown in SEQ ID NO: 10 in the sequence listing, which protein has a function of promoting growth in the presence of acetic acid; ("8") a DNA that encodes a protein shown in following (A), (B), or (C): (A) a protein having the amino acid sequence shown in SEQ ID NO: 10 in the sequence listing, (B) a protein consisting of an amino acid sequence comprising a substitution, deletion, insertion, addition, or inversion of one or several amino acids in the amino acid sequence shown in SEQ ID NO: 10 in the sequence listing, which protein has a function of promoting growth in the presence of acetic acid, (C) a protein consisting of an amino acid sequence having at least 85% or more homology to the amino acid sequence shown in SEQ ID NO: 10 in the sequence listing, which protein has a function of promoting growth in the presence of acetic acid; and ("9") a DNA of following (A), (B), (C), or (D): (A) a DNA consisting of the nucleotide sequence of nucleotide numbers 201 to 578 in the nucleotide sequence shown in SEQ ID NO: 9 in the sequence listing, (B) a DNA that hybridizes under stringent conditions with a DNA consisting of a sequence complementary to the nucleotide sequence of nucleotide numbers 201 to 578 in the nucleotide sequence shown in SEQ ID NO: 9 in the sequence listing, which DNA encodes a protein having a function of promoting growth in the presence of acetic acid, (C) a DNA that hybridizes under stringent conditions with a DNA consisting of a nucleotide sequence having a function as a primer or a probe that is produced from a part of the nucleotide sequence of nucleotide numbers 201 to 578 in the nucleotide sequence shown in SEQ ID NO: 9 in the sequence listing, which DNA encodes a protein having a function of promoting growth in the presence of acetic acid, (D) a DNA consisting of a nucleotide sequence comprising a substitution, deletion, insertion, addition, or inversion of one or several nucleotides in the nucleotide sequence of nucleotide numbers 201 to 578 in the nucleotide sequence shown in SEQ ID NO: 9 in the sequence listing, which DNA encodes a protein having a function of promoting growth in the presence of acetic acid.

Further, the present invention relates to: ("10") a protein of following (A), (B), or (C): (A) a protein consisting of the amino acid sequence shown in SEQ ID NO: 14 in the sequence listing, (B) a protein consisting of an amino acid sequence comprising a substitution, deletion, insertion, addition, or inversion of one or several amino acids in the amino acid sequence shown in SEQ ID NO: 14 in the sequence listing, which protein has a function of promoting growth in the presence of acetic acid, (C) a protein consisting of an amino acid sequence having at least 85% or more homology to the amino acid sequence shown in SEQ ID NO: 14 in the sequence listing, which protein has a function of promoting growth in the presence of acetic acid; ("11") a DNA that encodes a protein shown in following (A), (B), or (C): (A) a protein consisting of the amino acid sequence shown in SEQ ID NO: 14 in the sequence listing, (B) a protein consisting of an amino acid sequence comprising a substitution, deletion, insertion, addition, or inversion of one or several amino acids in the amino acid sequence shown in SEQ ID NO: 14 in the sequence listing, which protein has a function of promoting growth in the presence of acetic acid, (C) a protein consisting of an amino acid sequence having at least 85% or more homology to the amino acid sequence shown in SEQ ID NO: 14 in the sequence listing, which protein has a function of promoting growth in the presence of acetic acid; and ("12") a DNA of following (A), (B), (C), or (D): (A) a DNA consisting of the nucleotide sequence of nucleotide numbers 240 to 731 in the nucleotide sequence shown in SEQ ID NO: 13 in the sequence listing, (B) a DNA that hybridizes under stringent conditions with a DNA consisting of a sequence complementary to the nucleotide sequence of nucleotide numbers 240 to 731 in the nucleotide sequence shown in SEQ ID NO: 13 in the sequence listing, which DNA encodes a protein having a function of promoting growth in the presence of acetic acid, (C) a DNA that hybridizes under stringent conditions with a DNA consisting of a nucleotide sequence having a function as a primer or a probe that is produced from a part of the nucleotide sequence of nucleotide numbers 240 to 731 in the nucleotide sequence shown in SEQ ID NO: 13 in the sequence listing, which DNA encodes a protein having a function of promoting growth in the presence of acetic acid, (D) a DNA consisting of a nucleotide sequence comprising a substitution, deletion, insertion, addition, or inversion of one or several nucleotides in the nucleotide sequence of nucleotide numbers 240 to 731 in the nucleotide sequence shown in SEQ ID NO: 13 in the sequence listing, which DNA encodes a protein having a function of promoting growth in the presence of acetic acid.

Further, the present invention relates to: ("13") a protein of following (A), (B), or (C): (A) a protein consisting of the amino acid sequence shown in SEQ ID NO: 18 in the sequence listing, (B) a protein consisting of an amino acid sequence comprising a substitution, deletion, insertion, addition, or inversion of one or several amino acids in the amino acid sequence shown in SEQ ID NO: 18 in the sequence listing, which protein has a function of promoting growth in the presence of acetic acid, (C) a protein consisting of an amino acid sequence having at least 85% or more homology to the amino acid sequence shown in SEQ ID NO: 18 in the sequence listing, which protein has a function of promoting growth in the presence of acetic acid; ("14") a DNA that encodes a protein shown in following (A), (B), or (C): (A) a protein having the amino acid sequence shown in SEQ ID NO: 18 in the sequence listing, (B) a protein consisting of an amino acid sequence comprising a substitution, deletion, insertion, addition, or inversion of one or several amino acids in the amino acid sequence shown in SEQ ID NO: 18 in the sequence listing, which protein has a function of promoting growth in the presence of acetic acid, (C) a protein consisting of an amino acid sequence having at least 85% or more homology to the amino acid sequence shown in SEQ ID NO: 18 in the sequence listing, which protein has a function of promoting growth in the presence of acetic acid; and ("15") a DNA of following (A), (B), (C), or (D) (A) a DNA consisting of the nucleotide sequence of nucleotide numbers 201 to 761 in the nucleotide sequence shown in SEQ ID NO: 17 in the sequence listing, (B) a DNA that hybridizes under stringent conditions with a DNA consisting of a sequence complementary to the nucleotide sequence of nucleotide numbers 201 to 761 in the nucleotide sequence shown in SEQ ID NO: 17 in the sequence listing, which DNA encodes a protein having a function of promoting growth in the presence of acetic acid, (C) a DNA that hybridizes under stringent conditions with a DNA consisting of a nucleotide sequence having a function as a primer or a probe that is produced from a part of the nucleotide sequence of nucleotide numbers 201 to 761 in the nucleotide sequence shown in SEQ ID NO: 17 in the sequence listing, which DNA encodes a protein having a function of promoting growth in the presence of acetic acid, (D) a DNA consisting of a nucleotide sequence comprising a substitution, deletion, insertion, addition, or inversion of one or several nucleotides in the nucleotide sequence of nucleotide numbers 201 to 761 in the nucleotide sequence shown in SEQ ID NO: 17 in the sequence listing, which DNA encodes a protein having a function of promoting growth in the presence of acetic acid.

Further, the present invention relates to: ("16") a protein of following (A), (B), or (C): (A) a protein consisting of the amino acid sequence shown in SEQ ID NO: 22 in the sequence listing, (B) a protein consisting of an amino acid sequence comprising a substitution, deletion, insertion, addition, or inversion of one or several amino acids in the amino acid sequence shown in SEQ ID NO: 22 in the sequence listing, which protein has a function of promoting growth in the presence of acetic acid, (C) a protein consisting of an amino acid sequence having at least 85% or more homology to the amino acid sequence shown in SEQ ID NO: 22 in the sequence listing, which protein has a function of promoting growth in the presence of acetic acid; ("17") a DNA that encodes a protein shown in following (A), (B), or (C): (A) a protein having the amino acid sequence shown in SEQ ID NO: 22 in the sequence listing, (B) a protein consisting of an amino acid sequence comprising a substitution, deletion, insertion, addition, or inversion of one or several amino acids in the amino acid sequence shown in SEQ ID NO: 22 in the sequence listing, which protein has a function of promoting growth in the presence of acetic acid, (C) a protein consisting of an amino acid sequence having at least 85% or more homology to the amino acid sequence shown in SEQ ID NO: 22 in the sequence listing, which protein has a function of promoting growth in the presence of acetic acid; and ("18") a DNA of following (A), (B), (C), or (D): (A) a DNA consisting of the nucleotide sequence of nucleotide numbers 193 to 642 in the nucleotide sequence shown in SEQ ID NO: 21 in the sequence listing, (B) a DNA that hybridizes under stringent conditions with a DNA consisting of a sequence complementary to the nucleotide sequence of nucleotide numbers 193 to 642 in the nucleotide sequence shown in SEQ ID NO: 21 in the sequence listing, which DNA encodes a protein having a function of promoting growth in the presence of acetic acid, (C) a DNA that hybridizes under stringent conditions with a DNA consisting of a nucleotide sequence having a function as a primer or a probe that is produced from a part of the nucleotide sequence of nucleotide numbers 193 to 642 in the nucleotide sequence shown in SEQ ID NO: 21 in the sequence listing, which DNA encodes a protein having a function of promoting growth in the presence of acetic acid, (D) a DNA consisting of a nucleotide sequence comprising a substitution, deletion, insertion, addition, or inversion of one or several nucleotides in the nucleotide sequence of nucleotide numbers 193 to 642 in the nucleotide sequence shown in SEQ ID NO: 21 in the sequence listing, which DNA encodes a protein having a function of promoting growth in the presence of acetic acid.

Further, the present invention relates to: ("19") a protein of following (A), (B), or (C): (A) a protein consisting of the amino acid sequence shown in SEQ ID NO: 26 in the sequence listing, (B) a protein consisting of an amino acid sequence comprising a substitution, deletion, insertion, addition, or inversion of one or several amino acids in the amino acid sequence shown in SEQ ID NO: 26 in the sequence listing, which protein has a function of promoting growth in the presence of acetic acid, (C) a protein consisting of an amino acid sequence having at least 85% or more homology to the amino acid sequence shown in SEQ ID NO: 26 in the sequence listing, which protein has a function of promoting growth in the presence of acetic acid; ("20") a DNA that encodes a protein shown in following (A), (B), or (C): (A) a protein having the amino acid sequence shown in SEQ ID NO: 26 in the sequence listing, (B) a protein consisting of an amino acid sequence comprising a substitution, deletion, insertion, addition, or inversion of one or several amino acids in the amino acid sequence shown in SEQ ID NO: 26 in the sequence listing, which protein has a function of promoting growth in the presence of acetic acid, (C) a protein consisting of an amino acid sequence having at least 85% or more homology to the amino acid sequence shown in SEQ ID NO: 26 in the sequence listing, which protein has a function of promoting growth in the presence of acetic acid; and ("21") a DNA of following (A), (B), (C), or (D): (A) a DNA consisting of the nucleotide sequence of nucleotide numbers 228 to 773 in the nucleotide sequence shown in SEQ ID NO: 25 in the sequence listing, (B) a DNA that hybridizes under stringent conditions with a DNA consisting of a sequence complementary to the nucleotide sequence of nucleotide numbers 228 to 773 in the nucleotide sequence shown in SEQ ID NO: 25 in the sequence listing, which DNA encodes a protein having a function of promoting growth in the presence of acetic acid, (C) a DNA that hybridizes under stringent conditions with a DNA consisting of a nucleotide sequence having a function as a primer or a probe that is produced from a part of the nucleotide sequence of nucleotide numbers 228 to 773 in the nucleotide sequence shown in SEQ ID NO: 25 in the sequence listing, which DNA encodes a protein having a function of promoting growth in the presence of acetic acid, (D) a DNA consisting of a nucleotide sequence comprising a substitution, deletion, insertion, addition, or inversion of one or several nucleotides in the nucleotide sequence of nucleotide numbers 228 to 773 in the nucleotide sequence shown in SEQ ID NO: 25 in the sequence listing, which DNA encodes a protein having a function of promoting growth in the presence of acetic acid.

Further, the present invention relates to: ("22") a recombinant vector comprising one or more DNAs selected from DNAs according to the above ("2"), ("3"), ("5"), ("6"), ("8"), ("9"), ("11"), ("12"), ("14"), ("15"), ("17"), ("18"), ("20"), and ("21"); ("23") a transformant containing the recombinant vector according to the above ("22"); ("24") a microorganism wherein a function of promoting growth in the presence of acetic acid is enhanced by amplified intracellular copies of one or more DNAs selected from DNAs according to the above ("2"), ("3"), ("5"), ("6"), ("8"), ("9"), ("11"), ("12"), ("14"), ("15"), ("17"), ("18"), ("20"), and ("21"); ("25") the microorganism according to the above ("24"), which is an acetic acid bacterium belonging to the genus *Acetobacter* or the genus *Gluconacetobacter*; ("26") a method for producing vinegar comprising culturing the microorganism according to the above ("24") or ("25") in a medium containing alcohol and allowing acetic acid to form and accumulate in the medium; and ("27") vinegar obtained by the method according to the above ("26").

BRIEF DESCRIPTION OF DRAWINGS

FIG. 1 This figure shows a restriction map of a gene fragment cloned for spot AAR1, and a schematic view of the site of a gene having a function of promoting growth and of the fragment inserted into pPPI.

FIG. 2 This figure shows the amino acid sequence of the protein encoded by the nucleotide sequence of nucleotide numbers 213 to 764 in the nucleotide sequence shown in SEQ ID NO: 1.

FIG. 3 This figure shows primer 1. (SEQ ID NO: 3)

FIG. 4 This figure shows primer 2. (SEQ ID NO: 4)

FIG. 5 This figure shows a restriction map of a gene fragment cloned for spot AAR2, and a schematic view of the site of a gene having a function of promoting growth and of the fragment inserted into pSOD.

FIG. 6 This figure shows the amino acid sequence of the protein encoded by the nucleotide sequence of nucleotide numbers 231 to 836 in the nucleotide sequence shown in SEQ ID NO: 5.

FIG. 7 This figure shows primer 3. (SEQ ID NO: 7)

FIG. 8 This figure shows primer 4. (SEQ ID NO: 8)

FIG. 9 This figure shows a restriction map of a gene fragment cloned for spot AAR3, and a schematic view of the site of a gene having a function of promoting growth and of the fragment inserted into pUNK.

FIG. 10 This figure shows the amino acid sequence of the protein encoded by the nucleotide sequence of nucleotide numbers 201 to 576 in the nucleotide sequence shown in SEQ ID NO: 9.

FIG. 11 This figure shows primer 5. (SEQ ID NO: 11)

FIG. 12 This figure shows primer 6. (SEQ ID NO: 12)

FIG. 13 This figure shows a restriction map of a gene fragment cloned for spot AAR4, and a schematic view of the site of a gene having a function of promoting growth and of the fragment inserted into pYBH.

FIG. 14 This figure shows the amino acid sequence of the protein encoded by the nucleotide sequence of nucleotide numbers 240 to 731 in the nucleotide sequence shown in SEQ ID NO: 13.

FIG. 15 This figure shows primer 7. (SEQ ID NO: 15)

FIG. 16 This figure shows primer 8. (SEQ ID NO: 16)

FIG. 17 This figure shows a restriction map of a gene fragment cloned for spot AAR5, and a schematic view of the site of a gene having a function of promoting growth and of the fragment inserted into pAHR.

FIG. 18 This figure shows the amino acid sequence of the protein encoded by the nucleotide sequence of nucleotide numbers 201 to 761 in the nucleotide sequence shown in SEQ ID NO: 17.

FIG. 19 This figure shows primer 9. (SEQ ID NO: 19)

FIG. 20 This figure shows primer 10. (SEQ ID NO: 20)

FIG. 21 This figure shows a restriction map of a gene fragment cloned for spot AAR6, and a schematic view of the site of a gene having a function of promoting growth and of the fragment inserted into pUNK2.

FIG. 22 This figure shows the amino acid sequence of the protein encoded by the nucleotide sequence of nucleotide numbers 193 to 642 in the nucleotide sequence shown in SEQ ID NO: 21.

FIG. 23 This figure shows primer 11. (SEQ ID NO: 23)

FIG. 24 This figure shows primer 12. (SEQ ID NO: 24)

FIG. 25 This figure shows a restriction map of a gene fragment cloned for spot AAR7, and a schematic view of the site of a gene having a function of promoting growth and of the fragment inserted into pUNK3.

FIG. 26 This figure shows the amino acid sequence of the protein encoded by the nucleotide sequence of nucleotide numbers 228 to 773 in the nucleotide sequence shown in SEQ ID NO: 25.

FIG. 27 This figure shows primer 13. (SEQ ID NO: 27)

FIG. 28 This figure shows primer 14. (SEQ ID NO: 28)

FIG. 29 This figure shows the time-course of a culture of a transformant (pPPI).

FIG. 30 This figure shows the time-course of a culture of a transformant (pSOD).

FIG. 31 This figure shows the time-course of a culture of a transformant (pUNK).

FIG. 32 This figure shows the time-course of a culture of a transformant (pYBH).

FIG. 33 This figure shows the time-course of a culture of a transformant (pAHR).

FIG. 34 This figure shows the time-course of a culture of a transformant (pUNK2).

FIG. 35 This figure shows the time-course of a culture of a transformant (pUNK3).

BEST MODE OF CARRYING OUT THE INVENTION

The protein of the present invention is not particularly limited as long as it is a protein consisting of the amino acid sequence shown in SEQ ID NO: 2, 6, 10, 14, 18, 22, or 26 in the sequence listing: a protein consisting of an amino acid sequence comprising a substitution, deletion, insertion, addition, or inversion of one or several amino acids in the amino acid sequence shown in SEQ ID NO: 2, 6, 10, 14, 18, 22, or 26 in the sequence listing, which protein has a function of promoting growth in the presence of acetic acid, or a protein consisting of an amino acid sequence having at least 85% or more homology to the amino acid sequence shown in SEQ ID NO: 2, 6, 10, 14, 18, 22, or 26 in the sequence listing, which protein has a function of promoting growth in the presence of acetic acid. In the present invention, "a protein having a function of promoting growth in the presence of acetic acid" refers to a protein making an absorbance value at 660 nm more than twice as high as compared to the case of the untransformed original strain (parent strain) in the following measurement: inoculating 100 ml of YPG medium containing 3% ethanol and 3% acetic acid with a transformant provided by transforming the DNA encoding the protein into *Acetobacter aceti* No. 1023 strain by electroporation method; performing a shaking-culture (150 rpm) at 30° C. for 5 days; and measuring the absorbance value at 660 nm of the acetic acid-added YPG medium in which transformants have grown.

Further, the DNA of the present invention is not particularly limited as long as it is a DNA that encodes a protein consisting of the amino acid sequence shown in SEQ ID NO: 2, 6, 10, 14, 18, 22, or 26 in the sequence listing; a DNA that encodes a protein consisting of an amino acid sequence comprising a substitution, deletion, insertion, addition, or inversion of one or several amino acids in the amino acid sequence shown in SEQ ID NO: 2, 6, 10, 14, 18, 22, or 26 in the sequence listing, which protein has a function of promoting growth in the presence of acetic acid; a DNA that encodes a protein consisting of an amino acid sequence having at least 85% or more homology to the amino acid sequence shown in SEQ ID NO: 2, 6, 10, 14, 18, 22, or 26 in the sequence listing, which protein has a function of promoting growth in the presence of acetic acid; a DNA consisting of the nucleotide sequence of SEQ ID NO: 1 (nucleotide numbers 213 to 764), SEQ ID NO: 5 (nucleotide numbers 231 to 836), SEQ ID NO: 9 (nucleotide numbers 201 to 578), SEQ ID NO: 13 (nucleotide numbers 240 to 731), SEQ ID NO: 17 (nucleotide numbers 201 to 761), SEQ ID NO: 21 (nucleotide numbers 193 to 642), or SEQ ID NO: 25 (nucleotide numbers 228 to 773) in the sequence listing; a DNA that hybridizes under stringent conditions with a DNA consisting of a sequence complementary to the nucleotide sequence of SEQ ID NO: 1 (nucleotide numbers 213 to 764), SEQ ID NO: 5 (nucleotide numbers 231 to 836), SEQ ID NO: 9 (nucleotide numbers 201 to 578), SEQ ID NO: 13 (nucleotide numbers 240 to 731), SEQ ID NO: 17 (nucleotide numbers 201 to 761), SEQ ID NO: 21 (nucleotide numbers 193 to 642), or SEQ ID NO: 25 (nucleotide numbers 228 to 773) in the sequence listing, which DNA encodes a protein having a function of promoting growth in the presence of acetic acid; a DNA that hybridizes under stringent conditions with a DNA consisting of a nucleotide sequence having a function as a primer or a probe that is prepared from a part of the nucleotide sequence of SEQ ID NO: 1 (nucleotide numbers 213 to 764), SEQ ID NO: 5 (nucleotide numbers 231 to 836), SEQ ID NO: 9 (nucleotide numbers 201 to 578), SEQ ID NO: 13 (nucleotide numbers 240 to 731), SEQ ID NO: 17 (nucleotide numbers 201 to 761), SEQ ID NO: 21 (nucleotide numbers 193 to 642), or SEQ ID NO: 25 (nucleotide numbers 228 to 773) in the sequence listing, which DNA encodes a protein having a function of promoting growth in the presence of acetic acid; or a DNA consisting of a nucleotide sequence comprising a substitution, deletion, insertion, addition, or inversion of one or several nucleotides in the nucleotide sequence of SEQ ID NO: 1 (nucleotide numbers 213 to 764), SEQ ID NO: (nucleotide numbers 231 to 836), SEQ ID NO: 9 (nucleotide numbers 201 to 578), SEQ ID NO: 13 (nucleotide numbers 240 to 731), SEQ ID NO: 17 (nucleotide numbers 201 to 761), SEQ ID NO: 21 (nucleotide numbers 193 to 642), or SEQ ID NO: (nucleotide numbers 228 to 773) in the sequence listing, which DNA encodes a protein having a function of promoting growth in the presence of acetic acid. For example, the above expression such as "SEQ ID NO: 1 (nucleotide numbers 213 to 764)" means "nucleotide numbers 213 to 764 in the nucleotide sequence shown in SEQ ID NO: 1".

As stated above, a DNA that encodes a protein having a function of promoting growth in the presence of acetic acid of the present invention can be a DNA that encodes a protein comprising a substitution, deletion, insertion, addition, or inversion of one or several amino acids at one or more sites, as long as the function of enhancing acetic acid tolerance of the coded protein is not impaired. A DNA that encodes a protein that is substantially the same as the above-mentioned protein having a function of promoting growth in the presence of acetic acid can also be obtained by a modification of a nucleotide sequence, such modification being a substitution, deletion, insertion, addition, or inversion of an amino acid of a specific site by means of, for example, site-directed mutagenesis. Further, a modified DNA such as the above can also be obtained by a conventionally known spontaneous mutagenesis. Still further, it is possible to obtain a DNA that encodes substantially the same protein from acetic acid bacteria in general, in particular, from a species, strain, mutant, or variant of the genus *Acetobacter* or the genus *Gluconacetobacter*, because it is known that, in general, an amino acid sequence of a protein and an nucleotide sequence encoding the same are slightly different between the species, strains, mutants, or variants.

The above "an amino acid sequence comprising a substitution, deletion, insertion, addition, or inversion of one or several amino acids" means, for example, an amino acid sequence wherein any number of amino acids, for example, 1 to 20, preferably 1 to 15, more preferably 1 to 10, and still more preferably 1 to 5 amino acids, are substituted, deleted, inserted, added, or inverted. Further, the above "nucleotide sequence comprising a substitution, deletion, insertion, addition, or inversion of one or several nucleotides" means, for example, a nucleotide sequence wherein any number of nucleotides, for example, 1 to 20, preferably 1 to 15, more preferably 1 to 10, and still more preferably 1 to 5 nucleotides are substituted, deleted, inserted, added, or inverted.

For example, these DNAs consisting of a nucleotide sequence comprising a substitution, deletion, insertion, addition, or inversion of one or several nucleotides (mutated DNAs) can also be prepared by any method known to a skilled person in the art, such as chemical synthesis, genetic engineering technique, mutagenesis, as stated above. Specifically, mutated DNAs can be obtained by introducing a mutation into the DNAs consisting of the nucleotide sequence shown in SEQ ID NO: 1 (nucleotide numbers 213 to 764), SEQ ID NO: 5 (nucleotide numbers 231 to 836), SEQ ID NO: 9 (nucleotide numbers 201 to 578), SEQ ID NO: 13 (nucleotide numbers 240 to 731), SEQ ID NO: 17 (nucleotide numbers 201 to 761), SEQ ID NO: 21 (nucleotide numbers 193 to 642), or SEQ ID NO: 25 (nucleotide numbers 228 to 773) in the sequence listing, using a method of allowing a mutagenic agent to contact with and act on the DNA; a method of irradiating the DNA with ultraviolet light; a genetic engineering technique or the like. The site-directed mutagenesis, one of the genetic engineering techniques, is useful as it is a technique that allows an introduction of a specific mutation into a specific site, and can be performed according to the method described in Molecular Cloning, 2nd edition, Current Protocols in Molecular Biology, Supplement 1 to 38, John Wiley & Sons (1987 to 1997) or the like. An expression of this mutated DNA using an appropriate expression system provides a protein consisting of an amino acid sequence comprising a substitution, deletion, insertion, addition, or inversion of one or several amino acids.

The above "amino acid sequence having at least 85% or more homology to the amino acid sequence shown in SEQ ID NO: 2, 6, 10, 14, 18, 22, or 26" is not particularly limited as long as the homology to the amino acid sequence shown in SEQ ID NO: 2, 6, 10, 14, 18, 22, or 26 is 85% or more. This means that the homology is, for example, 85% or more, preferably 90% or more, more preferably 95% or more, and particularly preferably 98% or more.

The above "under stringent conditions" refers to a condition under which a so-called specific hybrid is formed while a non-specific hybrid is not formed. Specific examples include a condition under which DNAs having 50% to 70% or more homology hybridize while DNAs with lower homology do not hybridize; or a hybridization condition at a salt concentration corresponding to 1×SSC, 0.1% SDS, or 0.1×SSC, 0.1% SDS at 65° C., which is a washing condition of normal southern hybridization. Further, the above "DNA that hybridizes under stringent conditions" means a DNA that can be obtained by using a method such as a colony hybridization, plaque hybridization or southern-blot hybridization using a nucleic acid such as a DNA or RNA as a probe. Specific examples include a DNA that can be identified by subjecting a DNA or a fragment of the DNA derived from a colony or plaque to a hybridization at 65° C. in the presence of 0.7 to 1.0 M NaCl using a immobilized filter, followed by washing the filter using a 0.1 to 2-fold-concentration SSC solution (the composition of the one-fold-concentration SSC solution is: 150 mM sodium chloride and 15 mM sodium citrate) under the condition of 65° C. The hybridization can be performed according to the method described in Molecular Cloning: A laboratory Mannual, 2nd Ed., Cold Spring Harbor Laboratory, Cold Spring Harbor, N.Y., 1989 (hereinafter abridged as "Molecular Cloning, 2nd Ed.") or the like.

Examples of a DNA that can hybridize under stringent conditions include a DNA having a homology above a certain level to a nucleotide sequence of a DNA used as a probe. A DNA having a homology of, for example, 60% or more, preferably 70% or more, more preferably 80% or more, still more preferably 90% or more, particularly preferably 95% or more, and most preferably 98% or more, can be exemplified advantageously.

A method of obtaining or preparing a DNA of the present invention is not particularly limited. The DNA of interest can be isolated by preparing an appropriate probe or primer based on the nucleotide sequence information shown in SEQ ID NO: 1, 5, 9, 13, 17, 21, or 25 or amino acid sequence information shown in SEQ ID NO: 2, 6, 10, 14, 18, 22, or 26 disclosed herein, and using the probe or primer for screening a cDNA library where the DNA is expected to exist, or the DNA can be prepared by chemical synthesis according to a common method.

The genomic DNA of the present invention can be obtained, for example, by preparing a cDNA library according to a common method from acetic acid bacteria belonging to the genus *Acetobacter* or the genus *Gluconacetobacter*, and then selecting from this library a desired clone using an appropriate probe which is specific to the genomic DNA of the present invention. Further, the isolation of total RNA from these acetic acid bacteria, isolation and purification of mRNAs, preparation of cDNAs, cloning of the cDNAs and the like can all be performed according to a common method. Examples of a method of screening a genomic DNA of the present invention from a cDNA library include the methods commonly used by a skilled person in the art such as a method described in Molecular Cloning, 2nd ed.

Specifically, the DNA consisting of the nucleotide sequence shown in SEQ ID NO: 1, 5, 9, 13, 17, 21, or 25 of the present invention can be obtained as stated below from a chromosomal DNA of *Gluconacetobacter entanii*. First, a chromosomal DNA library is prepared for *Gluconacetobacter entanii*, for example, for *Acetobacter* altoacetigenes MH-24 strain (FERM BP-491). Meanwhile, the chromosomal DNA is obtained by a common method (for example, see Japanese Laid-Open Patent Application No. 60-9489). Next, in order to isolate a gene having a function of promoting growth from the obtained chromosomal DNA, a chromosomal DNA library is prepared. First, the chromosomal DNA is partially digested with appropriate restriction enzymes to obtain a mixture of various fragments. An adjustment of the degree of fragmentation by adjusting the reaction time and the like allows the use of a wide variety of restriction enzymes. For example, Sau3AI is allowed to act on and digest the chromosomal DNA at the temperature of 30° C. or above, preferably at 37° C., at an enzyme concentration of 1 to 10 units/ml for various durations (1 minute to 2 hours). Next, the digested chromosomal DNA fragments are ligated to a vector DNA capable of replicating autonomously in acetic acid bacteria, to produce a recombinant vector. Specifically, a restriction enzyme is used that produces a terminal nucleotide sequence which is complementary to the sequence produced by restriction enzyme Sau3AI used for the digestion of the chromosomal DNA. For example, BamHI is allowed to act on the vector DNA for 1 hour or more under the condition of the temperature of 30° C. at an enzyme concentration of 1 to 100 units/ml, to completely digest and cleave the vector DNA. Then the mixture of chromosomal DNA fragments obtained as stated above is mixed with the digested and cleaved vector DNA. $T_4$DNA ligase is allowed to act on this mixture under the condition of a temperature of 4 to 16° C., at an enzyme concentration of 1 to 100 units/ml for 1 hour or more, preferably for 6 to 24 hours to obtain a recombinant vector. The DNA of the obtained recombinant vector is mixed with *Escherichia coli* JM109 competent cells. The mixture is left for 10 minutes at 0° C., and heated at 42° C. for 45 seconds for the cells to be incorporated into the DNA. To these cells, SOC medium is added, and the mixture is shaking-cultured for 1 hour and then spread on an LB agar plate medium containing 100 μg/ml ampicillin, followed by a culture at 37° C. overnight. Bacteria forming a white colony on this plate medium are selected as transformants. Further, from the obtained transformants, positive transformants are obtained by using the gene prepared from the N-terminal amino acid sequence of a protein identified to have an acetic acid torelence as a DNA probe, labeling the probe with digoxigenin, and performing a colony hybridization.

Further, the mutant gene or homologous gene of the present invention consisting of: a DNA that encodes a protein consisting of an amino acid sequence comprising a substitution, deletion, insertion, addition, or inversion of one or several amino acids in the above amino acid sequence shown in SEQ ID NO: 2, 6, 10, 14, 18, 22, or 26 in the sequence listing, which protein has a function of promoting growth in the presence of acetic acid; or a DNA that encodes a protein consisting of an amino acid sequence having at least 85% or more homology to the amino acid sequence shown in SEQ ID NO: 2, 6, 10, 14, 18, 22, or 26 in the sequence listing, which protein has a function of promoting growth in the presence of acetic acid, can be isolated from other acetic acid bacteria or the like by screening homologues of the DNA, under an appropriate condition utilizing a DNA fragment having the nucleotide sequence or a part of the nucleotide sequence shown in SEQ ID NO: 1, 5, 9, 13, 17, 21, or 25. In addition, the preparation is possible by the aforementioned method of producing a mutated DNA.

A DNA that encodes a protein substantially the same as the above protein can be obtained by isolating a DNA that encodes a protein having a function of promoting growth and that hybridizes under stringent conditions with a probe produced from, for example: acetic acid bacteria belonging to the genus *Acetobacter* or the genus *Gluconacetobacter*; mutated acetic acid bacteria belonging to the genus *Acetobacter* or the genus *Gluconacetobacter*; or a natural mutant strain or variant of the above acetic acid bacteria. For example, the above probe is produced from the nucleotide sequence or a part of the nucleotide sequence shown in SEQ ID NO: 1 (nucleotide numbers 213 to 764), SEQ ID NO: 5 (nucleotide numbers 231 to 836), SEQ ID NO: 9 (nucleotide numbers 201 to 578), SEQ ID NO: 13 (nucleotide numbers 240 to 731), SEQ ID NO: 17 (nucleotide numbers 201 to 761), SEQ ID NO: 21 (nucleotide numbers 193 to 642), or SEQ ID NO: 25 (nucleotide numbers 228 to 773) in the sequence listing.

The method of obtaining and preparing the protein of the present invention is not particularly limited and the protein may be any of a naturally-derived protein, chemically synthesized protein, or genetically engineered recombinant protein. When obtaining a naturally-derived protein, the protein of the present invention can be obtained by combining appropriately the methods of isolating and purifying the protein from microorganism-cells that are expressing the protein. When preparing the protein by chemical synthesis, the protein of the present invention can be synthesized according to a chemical synthesis method such as Fmoc method (fluorenylmethyloxycarbonyl method) and tBOC method (t-butyloxycarbonyl method).

In addition, the protein of the present invention can be synthesized utilizing various types of commercially-available peptide synthesizers. When preparing the protein by a genetic engineering technique, the protein of the present invention can be prepared by introducing a DNA consisting of a nucleotide sequence encoding the protein into a preferable expression system. Among these approaches of preparation, genetic engineering technique is preferred since it is capable of preparing the protein in large amounts by a relatively easy operation.

For example, when preparing the protein of the present invention by a genetic engineering technique, known methods are used for recovering and purifying the protein from a cell culture, examples of which methods include ammonium sulfate or ethanol precipitation; acid extraction; anion- or cation-exchange chromatography; phosphocellulose chromatography; hydrophobic interaction chromatography; affinity chromatography; hydroxyapatite chromatography; and lectin chromatography. Preferably, high-speed liquid chromatography is employed. Examples of columns particularly used for affinity chromatography include a column to which antibodies such as monoclonal antibodies against the protein of the present invention are bound. When a usual peptide tag has been added to the protein of the present invention, the purified product of the protein can be obtained by using a column to which a substance having an affinity to the peptide tag is bound.

Further, a person skilled in the art can prepare or obtain as desired a protein consisting of an amino acid sequence comprising a substitution, deletion, insertion, addition, or inversion of one or several amino acids in the amino acid sequence shown in SEQ ID NO: 2, 6, 10, 14, 18, 22, or 26; or a protein consisting of an amino acid sequence having at least 85% or more homology to the amino acid sequence shown in SEQ ID NO: 2, 6, 10, 14, 18, 22, or 26, based on the information on the nucleotide sequence shown in SEQ ID NO: 1 (nucleotide numbers 213 to 764), SEQ ID NO: 5 (nucleotide numbers 231 to 836), SEQ ID NO: 9 (nucleotide numbers 201 to 578), SEQ ID NO: 13 (nucleotide numbers 240 to 731), SEQ ID NO: 17 (nucleotide numbers 201 to 761), SEQ ID NO: 21 (nucleotide numbers 193 to 642), or SEQ ID NO: 25 (nucleotide numbers 228 to 773), which sequences show an example of a nucleotide sequence encoding the amino acid sequence shown in SEQ ID NO: 2, 6, 10, 14, 18, 22, or 26, respectively. For example, the homologous DNA can be isolated from acetic acid bacteria belonging to the genus *Acetobacter*, the genus *Gluconacetobacter*, or from other acetic acid bacteria by the hybridization that uses a probe prepared by the polymerase chain reaction (PCR reaction) that uses as a primer an oligonucleotide synthesized based on the nucleotide sequence shown in SEQ ID NO: 1 (nucleotide numbers 213 to 764), SEQ ID NO: 5 (nucleotide numbers 231 to 836), SEQ ID NO: 9 (nucleotide numbers 201 to 578), SEQ ID NO: 13 (nucleotide numbers 240 to 731), SEQ ID NO: 17 (nucleotide numbers 201 to 761), SEQ ID NO: 21 (nucleotide numbers 193 to 642), or SEQ ID NO: 25 (nucleotide numbers 228 to 773); or by the synthesized oligonucleotide based on the above nucleotide sequences; and then screening under an appropriate condition. The full-length DNA of the homologous DNA is cloned, then integrated into an expression vector, and expressed in an appropriate host, thereby the protein encoded by the homologue DNA can be produced.

An oligonucleotide can be synthesized according to a conventional method using, for example, various commercially-available DNA synthesizers. Further, a PCR reaction can be performed according to a conventional method using a thermal cycler, GENEAMP® PCR System 2400 manufactured by Applied Biosystems, with the use of TAQ™ DNA polymerase (Takara Bio Inc.) or KOD PLUS™ (Toyobo Co., Ltd.).

It is also possible to bind the above protein of the present invention with a marker protein and/or a peptide tag to provide a fusion protein. The marker protein is not particularly limited, as long as it is a conventionally known marker protein. Specific examples of the marker protein include enzymes such as alkaline phosphatase and HRP, the Fc region of an antibody, a fluorescent material such as GFP. Further, specific examples of the peptide tag include conventionally known peptide tags including epitope tags such as HA, FLAG, Myc; and affinity tags such as GST, maltose-binding protein, biotinated peptide, and oligohistidine. The fusion protein can be produced by a common method, and is useful for a purification of the protein of the present invention, a detection of the protein of the present invention, and a quantification of an antibody against the protein of the present invention utilizing the affinity of Ni-NTA and His tag. The fusion protein is also useful as a laboratory reagent in the field to which the present invention pertains.

The recombinant vector of the present invention is not particularly limited as long as the recombinant vector comprises one or more kinds of the above DNA of the present invention, and is capable of expressing the protein having a function of promoting growth in the presence of acetic acid. The recombinant vector of the present invention can be constructed by appropriately integrating the DNA of the present invention into an expression vector. Preferred expression vectors are those capable of replicating autonomously in a host cell, or those that can be integrated into a chromosome of a host cell. Further, an expression vector containing a regulatory sequence such as a promoter, enhancer, or terminator at an appropriate site capable of expressing the DNA of the present invention can be used preferably.

Examples of an expression vector for bacteria include, acetic acid bacteria—*Escherichia coli* shuttle vector (a multicopy vector) pGI18 (for example, see Japanese Laid-Open Patent Application No. 2005-110597), pMV24 (for example, see Japanese Laid-Open Patent Application No. 61-58584), pTA5001(A), pTA5001(B) (for example, see Japanese Laid-Open Patent Application No. 60-9488), and pMVL1 (for example, see Agricultural and Biological Chemistry, Vol. 52, pp. 3125-3129, 1988). Ather examples include pBTrp2, pBTac1, pBTac2 (all commercially available from Boehringer Mannheim), pKK233-2 (Pharmacia), pSE280 (Invitrogen), pGEMEX-1 (Promega), pQE-8 (QIAGEN), pQE-30 (QIAGEN), pKYP10 (Japanese Laid-Open Patent Application No. 58-110600), pKYP200 [Agrc. Biol. Chem., 48, 669 (1984)], PLSA1 [Agrc. Blol. Chem., 53, 277 (1989)], pGEL1 [Proc. Natl. Acad. Sci. USA, 82, 4306 (1985)], pBluescriptII SK(+), pBluescriptII SK(−) (Stratagene), pTrS30 (FERMBP-5407), pTrS32 (FERMBP-5408), pGEX (Pharmacia), pET-3 (Novagen), pTerm2 (U.S. Pat. No. 4,686,191, U.S. Pat. No. 4,939,094, U.S. Pat. No. 5,160,735), pSupex, pUB110, pTP5, pC194, pUC18 [Gene, 33, 103 (1985)], pUC19 [Gene, 33, 103 (1985)], pSTV28 (Takara Bio), pSTV29 (Takara Bio), pUC118 (Takara Bio), pQE-30 (QIAGEN) and the like. Examples of a promoter for bacteria include promoters derived from *Escherichia coli*, phage or the like such as trp promoter (Ptrp), lac promoter (Plac), PL promoter, PR promoter, and PSE promoter; SP01 promoter, SP02 promoter, penP promoter and the like.

The transformant of the present invention is not particularly limited as long as it is a host cell comprising the above recombinant vector of the present invention, and is capable of expressing a protein having a function of promoting growth in the presence of acetic acid. Examples of the above host cell include bacteria, yeast, insect cells, and animal or plant cells, while bacteria are preferred. Among bacteria, acetic acid bacteria belonging to the genus *Acetobacter* or the genus *Gluconacetobacter* are particularly preferred. In addition to acetic acid bacteria belonging to the genus *Acetobacter* or the genus *Gluconacetobacter*, further examples of the host cell include microorganisms belonging to the genus *Escherichia*, the genus *Corynebacterium*, the genus *Brevibacterium*, the genus *Bacillus*, the genus *Microbacterium*, the genus *Serratia*, the genus *Pseudomonas*, the geneus *Agrobacterium*, the genus *Arthrobacter*, the genus *Erwinia*, the genus *Methylobacterium*, the genus *Rhodobacter*, the genus *Streptomyces*, the genus *Zymomonas* or the like. Examples of a method for introducing a recombinant vector into a bacterial host include, the calcium chloride method (for example, see Agricultural and Biological Chemistry, Vol. 49, pp. 2091-2097, 1985), the electroporation method (Proceedings of the National Academy of Sciences of the United States of America, Vol. 87, pp. 8130-8134, 1990), the protoplast method and the like. As a preferred transformant of the present invention, a transformant that is obtained by introducing into *Acetobacter aceti* No. 1023 strain (FERM BP-2287) a recombinant vector consisting of acetic acid bacteria—*Escherichia coli* shuttle vector (multicopy vector)pGI18 inserted with a DNA fragment, can be specifically exemplified.

The microorganism of the present invention is not particularly limited as long as it is a microorganism with an enhanced function of promoting growth in the presence of acetic acid, due to amplified intracellular copies of one or more DNA selected from the above DNAs of the present invention. Acetic acid bacteria belonging to the genus *Acetobacter* or the genus *Gluconacetobacter* with enhanced function of promoting growth in the presence of acetic acid are particularly preferred. In addition to acetic acid bacteria belonging to the genus *Acetobacter* or the genus *Gluconacetobacter*, examples of the microorganism of the present invention further include microorganisms belonging to the genus *Escherichia*, the genus *Corynebacterium*, the genus *Brevibacterium*, the genus *Bacillus*, the genus *Microbacterium*, the genus *Serratia*, the genus *Pseudomonas*, the geneus *Agrobacterium*, the genus *Arthrobacter*, the genus *Erwinia*, the genus *Methylobacterium*, the genus *Rhodobacter*, the genus *Streptomyces*, the genus *Zymomonas* or the like.

A specific example of the above acetic acid bacteria belonging to the genus *Acetobacter* is *Acetobacter aceti*, which is preferably exemplified by *Acetobacter aceti* No.

1023 strain (deposited with the International Patent Organism Depositary (IPOD) AIST (Address: Tsukuba Central 6, 1-1, Higashi 1-Chome, Tsukuba-shi, Ibaraki-Ken, 305-8566 Japan) on Feb. 13, 1989, as deposit number: FERM BP-2287). Further, a specific example of acetic acid bacteria belonging to the genus Gluconacetobacter is Gluconacetobacter entanii, which is preferably exemplified by Acetobacter altoacetigenes MH-24 strain presently deposited as FERM BP-491 with the International Patent Organism Depositary (IPOD) AIST (Address: Tsukuba Central 6, 1-1, Higashi 1-Chome, Tsukuba-shi, Ibaraki-Ken, 305-8566 Japan) (Date of deposit: Feb. 23, 1984).

Enhancing acetic-acid tolerance in acetic acid bacteria belonging to the genus Acetobacter or the genus Gluconacetobacter capable of oxidizing alcohol, will result in an increased acetic-acid production level and production efficiency. The function of promoting growth can be enhanced, for example, by amplifying the number of intracellular copies of a gene having a function of promoting growth, or by transforming bacteria belonging to the genus Acetobacter and or like using a recombinant DNA that can be obtained by linking a DNA fragment comprising a structural gene of the gene having a function of promoting growth, to a promoter sequence that functions efficiently in bacteria belonging to the genus Acetobacter. Further, an enhanced function of promoting growth in the presence of a high concentration of acetic acid is also achieved by substituting the promoter sequence of the gene on the chromosomal DNA for another promoter sequence that functions efficiently in acetic acid bacteria belonging to the genus Acetobacter or the genus Gluconacetobacter, for example, a promoter sequence derived from microorganisms other than acetic acid bacteria, such as the promoter of each of the following genes: ampicillin-resistance gene of plasmid pBR322 (Takara Bio), kanamycin-resistance gene of plasmid pHSG298 (Takara Bio), chloramphenicol-resistance gene of plasmid pHSG396 (Takara Bio), or β-galactosidase gene of Escherichia coli. Further, the intracellular copy numbers of the genes can be amplified by introducing a multi-copy vector retaining the gene into cells of bacteria belonging to the genus Acetobacter. More specifically, the amplification can be performed by introducing plasmid, transposon or the like retaining the gene into cells of acetic acid bacteria belonging to the genus Acetobacter or the genus Gluconacetobacter. Examples of the multi-copy vector include pGI18, pMV24, pTA5001 (A), pTA5001 (B) and the like as well as pMVL1 that is a chromosomal integration vector, and examples of transposon include Mu, IS1452 and the like.

The method for producing vinegar of the present invention is not particularly limited as long as the method comprises the steps of culturing the above microorganism of the present invention in a culture medium containing alcohol, and allowing acetic acid to form and accumulate in the culture medium. As the above microorganism, acetic acid bacteria belonging to the genus Acetobacter or the genus Gluconacetobacter are particularly preferred. Vinegar containing a high concentration of acetic acid can be produced efficiently, for example, by culturing the microorganism of the present invention having an alcohol oxidation ability in an alcohol-containing medium to allow acetic acid to form and accumulate in the culture medium, which microorganism is acetic acid bacteria belonging to the genus Acetobacter or the genus Gluconacetobacter in which a function of promoting growth is enhanced selectively due to the amplified copies of a gene having a function of promoting growth in the presence of a high concentration of acetic acid. Further, acetic acid fermentation in the method for producing vinegar of the present invention may be performed in a similar manner as the method for producing vinegar by a conventional method of fermenting acetic acid bacteria. The culture medium used for the acetic acid fermentation may be either a synthetic medium or a natural medium as long as it contains a carbon source, nitrogen source, inorganic substance, ethanol, and if necessary, an appropriate amount of nutrient source required for growth of bacterial strain in use. Examples of the above carbon source include various carbonhydrates, including glucose and sucrose, and various organic acids. As a nitrogen source, a natural nitrogen source such as peptone, fermented-bacteria degradation product or the like can be used. Further, the culture is performed under an aerobic condition such as in a static culture, shaking culture, aeration-agitation culture and the like. The culture is generally performed at the temperature of 30° C. The pH of medium is generally within the range of 2.5 to 7, preferably within the range of 2.7 to 6.5, and the pH can also be adjusted with various acids, various bases, buffers or the like. Generally, a 1- to 21-day culture can accumulate a high concentration of acetic acid in the medium.

The present invention further relates to vinegar obtained by the method for producing vinegar of the present invention.

The present invention will be explained more specifically with reference to the following examples, while the technical scope of the present invention will not be limited to these examples or the like.

Example 1

Cloning of a Genomic DNA that Encodes a Protein having a Function of Promoting Growth from Gluconacetobacter entanii and Determination of the Nucleotide Sequence and the Amino Acid Sequence (1) Identification of Acetic Acid-Stable Protein Bacterial cells of Acetobacter altoacetigenes MH-24 strain (deposited as FERM BP-491), which is a strain of Gluconacetobacter entanii, were disrupted with a French press, and the lysate was subjected to a centrifugation (7,500×g, 10 minutes) to remove intact bacterial cells to provide a supernatant. In order to extract from the supernatant a protein that is stable to acetic acid, acetic acid adjusted to pH 4.0 was added to the supernatant to the final concentration of 1 M. Proteins that became insoluble due to the addition of acetic acid were removed by centrifugation (7,500×g, 10 minutes), and a clear supernatant containing a protein that is soluble even in the presence of acetic acid and is stable to acetic acid was obtained.

The obtained supernatant was subjected to an isoelectric focusing electrophoresis in the first dimension, at an isoelectric point of pI3 to 10 (7 cm, pH 3 to 10, BIO-RAD) and to an electrophoresis in the second dimension using SDSPAGE (PAGE1™, 5 to 12.5% gradient gel). From the obtained SDS-PAGE gel, protein was transcripted onto a PVDF membrane (SEQUI-BLOT™ PVDH membrane, Bio-Rad) by performing a semi-dry type (AE-6677, Atto) western blotting. Consequently, major 10 spots, spots AAR1 to AAR10, were detected as shown in Table 1. Each spot transcripted onto the PVDF membrane was cut out and the N-terminal amino acid sequence of each spot was identified by an amino-acid sequencer (Applied Biosystems). Table 1 shows the summary of the isoelectric point, molecular weight, and N-terminal-side amino acid sequence for the 10 spots.

TABLE 1

| Spot name | SEQUENCE ID Location | Isoelectric point | Molecular Weight | N-terminal-side amino acid sequence |
|---|---|---|---|---|
| AAR1 | Residues 1-10 of SEQ ID NO: 2 | 6.0-7.0 | 18 KDa | Met-Asp-Arg-Gly-Arg-Leu-Ser-Gly-Pro-Val |
| AAR2 | Residues 1-10 of SEQ ID NO: 6 | 6.0-7.0 | 23 KDa | Met-Ala-Phe-Glu-Leu-Pro-Ser-Leu-Pro-Phe |
| AAR3 | Residues 1-10 of SEQ ID NO: 10 | 6.0-7.0 | 14 KDa | Met-Ser-Tyr-Val-Asp-Pro-Ala-Trp-Tyr-Val |
| AAR4 | Residues 1-10 of SEQ ID NO: 14 | 4.5-5.5 | 17 KDa | Met-Thr-Phe-Thr-Leu-Thr-Ser-Arg-Ser-Phe |
| AAR5 | Residues 1-10 of SEQ ID NO: 18 | 4.5-5.5 | 21 KDa | Met-Ala-Arg-Ile-Asn-Ser-Ser-Leu-Lys-Pro |
| AAR6 | Residues 1-10 of SEQ ID NO: 22 | 9.0-10.0 | 17 KDa | Met-Ser-Gly-Ala-Arg-Gln-Lys-Lys-Arg-Arg |
| AAR7 | Residues 1-10 of SEQ ID NO: 26 | 4.5-5.5 | 19 KDa | Met-Glu-Tyr-Pro-Met-Ser-Asp-Leu-Ile-Val |
| AAR8 | SEQ ID NO: 29 | 6.0-7.0 | 21 KDa | Met-Asp-Gln-Glu-Ser-Lys-Arg-Arg-Ala-Thr |
| AAR9 | SEQ ID NO: 30 | 5.0-6.0 | 33 KDa | Met-Arg-Ser-Ile-Arg-Ile-Met-Ala-Gln-Ile |
| AAR10 | SEQ ID NO: 31 | 5.0-6.0 | 27 KDa | Met-Ser-Arg-His-Arg-Ala-Arg-Arg-Lys-Gly |

(2) Preparation of Chromosomal DNA Library

*Acetobacter* altoacetigenes MH-24 strain (FERM BP-491), a strain of *Gluconacetobacter entanii*, was shaking-cultured in a YPG medium (3% glucose, 0.5% yeast extract, 0.2% polypeptone) added with 6% acetic acid and 4% ethanol at 30° C. After the culture, the culture medium was centrifuged (7,500×g, 10 minutes) to obtain bacteria. From the obtained bacteria, chromosomal DNA was prepared by a chromosomal DNA preparation method (for example, see Japanese Laid-Open Patent Application No. 60-9489).

The chromosomal DNA obtained as stated above was partially digested with the restriction enzyme Sau3AI (Takara Bio), and *Escherichia coli*—acetic acid shuttle vector pGI18 was completely digested and fragmented with the restriction enzyme BamHI. Appropriate amounts of each of these DNAs were mixed, ligated using a ligation kit (Takara DNA Ligation Kit Ver. 2, Takara Bio), transformed into *Escherichia coli* JM109 strain, and then selected on an LB agar medium containing 100 μg/ml ampicillin. Emerged colonies were subjected to a colony-hybridization using a probe (table 2) produced based on the amino acid sequence identified in the above (1) and labeled with digoxigenin, to obtain 7 strains of positive transformant (AAR1 to AAR7).

TABLE 2

| Spot name | Nucleotide sequence e for prob | SEQ ID Reference |
|---|---|---|
| AAR1 | ATGGACCGGGGCCGCCTGTCTGGTCCCGTT | Nucleotides 213-242 of Seq ID NO: 1 |
| AAR2 | ATGGCTTTCGAATTGCCGTCCCTTCCCTTC | Nucleotides 231-255 of SEQ ID NO: 5 |
| AAR3 | ATGAGTTATGTCGATCCTGCCTGGTATGTT | Nucleotides 201-230 of SEQ ID NO: 9 |
| AAR4 | ATGACGTTTACACTGACAAGCCGCTCCTTC | Nucleotides 240-269 of SEQ ID NO: 13 |
| AAR5 | ATGGCACGCATCAATTCGTCTCTGAAGCCG | Nucleotides 201-230 of SEQ ID NO: 17 |
| AAR6 | ATGAGCGGAGCGCGCCAGAAGAAGAGGCGG | Nucleotides 193-222 of SEQ ID NO: 21 |
| AAR7 | ATGGAGTATCCCATGTCCGATCTGATCGTT | Nucleotides 228-257 of SEQ ID NO: 25 |
| AAR8 | GTGGATCAGGAATCAAAAAGGAGGCCACA | SEQ ID NO: 32 |
| AAR9 | GTGAGGAGTATCAGGATAATGGCGCAGATT | SEQ ID NO: 33 |
| AAR10 | ATGTCTCGACATCGTGCGAGGAGGAAGGGT | SEQ ID NO: 34 |

(3) Determination of the Nucleotide Sequence of a Cloned DNA Fragment

1. Regarding Spot AAR1

The above cloned Sau3AI fragment was inserted into the BamHI site of pUC19, and the nucleotide sequence of the fragment was determined to be the nucleotide sequence described in SEQ ID NO: 1 as a result of the Sanger's dideoxy chain termination method. The sequence was determined for all regions of both DNA strands, by overlapping all the section points.

It was confirmed that, from nucleotide number 213 through nucleotide number 764 in the nucleotide sequence shown in SEQ ID NO: 1, there exists an open-reading frame that encodes 184 amino acids (FIG. 2) as described in SEQ ID NO: 2. Incidentally, a DNA including the nucleotide sequence consisting of nucleotide numbers 213 to 764 of SEQ ID NO: 1 has 79% homology to PPIase of *Gluconobacter oxydans*, and the PPIase is considered to fold a protein or to be functioning like a chaperone in cells. It is, however, not at all known to date whether the gene is related to a function of promoting growth.

Further, the N-terminal-side amino-acid sequence of the protein described in SEQ ID NO: 2 was Met-Asp-Arg-Gly-Arg-Leu-Ser-Gly-Pro-Val. This sequence was confirmed to correspond to the N-terminal-side amino acid sequence of the above protein, determined beforehand by the amino acid sequencing.

2. Regarding Spot AAR2

The above cloned Sau3AI fragment was inserted into the BamHI site of pUC19, and the nucleotide sequence of the fragment was determined to be the nucleotide sequence described in SEQ ID NO: 5 as a result of the Sanger's dideoxy chain termination method. The sequence was determined for all regions of both DNA strands, by overlapping all the section points.

It was confirmed that, from nucleotide number 231 through nucleotide number 836 in the nucleotide sequence shown in SEQ ID NO: 5, there exists an open-reading frame to encode 202 amino acids as described in SEQ ID NO: 6 (FIG. 6). Incidentally, the DNA including the nucleotide sequence consisting of nucleotide numbers 231 to 836 of SEQ ID NO: 5 shows 80% homology to SOD of *Gluconobacter oxydans*, and the SOD is considered to be involved in an anti-oxidant function. It is, however, not at all known to date whether the SOD is related to a function of promoting growth.

Further, the N-terminal-side amino-acid sequence of the protein described in SEQ ID NO: 6 was Met-Ala-Phe-Glu-Leu-Pro-Ser-Leu-Pro-Phe. This sequence was confirmed to correspond to the N-terminal-side amino acid sequence of the above protein, determined beforehand by the amino acid sequencing.

3. Regarding Spot AAR3

The above cloned Sau3AI fragment was inserted into the BamHI site of pUC19, and the nucleotide sequence of the fragment was determined to be the nucleotide sequence described in SEQ ID NO: 9 as a result of the Sanger's dideoxy chain termination method. The sequence was determined for all regions of both DNA strands, by overlapping all the section points.

It was confirmed that, from nucleotide number 201 through nucleotide number 578 in the nucleotide sequence shown in SEQ ID NO: 9, there exists an open-reading frame to encode 126 amino acids (FIG. 10) as described in SEQ ID NO: 10.

Further, the N-terminal-side amino acid sequence of the protein described in SEQ ID NO: 10 was Met-Ser-Tyr-Val-Asp-Pro-Ala-Trp-Tyr-Val. This sequence was confirmed to correspond to the N-terminal-side amino acid sequence of the above protein, determined beforehand by the amino acid sequencing. Incidentally, a DNA including the nucleotide sequence consisting of nucleotide numbers 201 to 578 shows 28% homology to the gene of Magnetospirillum magnetotacticum at the amino acid sequence level, and shows 23% homology to the gene of *Nitrosomonas europaea* at the amino acid sequence level, from which, it was estimated that the gene was encoding a protein. However, due to the very low degrees of homology, it was confirmed that the gene was a novel gene UNK that encodes a novel protein which is specific to acetic acid.

4. Regarding Spot AAR4

The above cloned Sau3AI fragment was inserted into the BamHI site of pUC19, and the nucleotide sequence of the fragment was determined to be the nucleotide sequence described in SEQ ID NO: 13 as a result of the Sanger's dideoxy chain termination method. The sequence was determined for all regions of both DNA strands, by overlapping all the section points.

It was confirmed that, from nucleotide number 240 through nucleotide number 731 in the nucleotide sequence shown in SEQ ID NO: 13, there exists an open-reading frame to encode 164 amino acids as described in SEQ ID NO: 14 (FIG. 14). Further, the N-terminal-side amino acid sequence of the protein described in SEQ ID NO: 14 was Met-Thr-Phe-Thr-Leu-Thr-Ser-Arg-Ser-Phe. This sequence was confirmed to correspond to the N-terminal-side amino acid sequence of the above protein, determined beforehand by the amino acid sequencing.

Incidentally, a DNA including the nucleotide sequence consisting of nucleotide numbers 240 to 731 shows 63% homology to the ybhB gene of *Escherichia coli* at the amino acid sequence level, and shows 62% homology to the gene of *Shigella flexneri* at the amino acid sequence level, from which, it was estimated that the gene was encoding a protein. However, the function of the gene has not been revealed even in other microorganisms, and it is not at all known to date whether the gene is related to a function of promoting growth.

5. Regarding Spot AAR5

The above cloned Sau3AI fragment was inserted into the BamHI site of pUC19, and the nucleotide sequence of the fragment was determined to be the nucleotide sequence described in SEQ ID NO: 17 as a result of the Sanger's dideoxy chain termination method. The sequence was determined for all regions of both DNA strands, by overlapping all the section points.

It was confirmed that, from nucleotide number 201 through nucleotide number 761 in the nucleotide sequence shown in SEQ ID NO: 17, there exists an open-reading frame to encode 187 amino acids as described in SEQ ID NO: 18 (FIG. 18). Further, the N-terminal-side amino acid sequence of the protein described in SEQ ID NO: 18 was Met-Ala-Arg-Ile-Asn-Ser-Ser-Leu-Lys-Pro. This sequence was confirmed to correspond to the N-terminal-side amino acid sequence of the above protein, determined beforehand by the amino-acid sequencing.

Incidentally, a DNA including the nucleotide sequence consisting of nucleotide numbers 201 to 761 shows 74% homology to the gene of alkyl-hydroperoxide reductase (hereinafter, sometimes referred to as AHD) of *Pseudomonas syringae* at the amino acid sequence level, and shows 67% homology to the gene of *Caulobacter crescentus* at the amino acid sequence level. AHD is generally considered to be involved in peroxide metabolization. It is, however, not at all known whether the gene is involved in the function of promoting growth in the presence of a high concentration of acetic acid.

6. Regarding Spot AAR6

The above cloned Sau3AI fragment was inserted into the BamHI site of pUC19, and the nucleotide sequence of the fragment was determined to be the nucleotide sequence described in SEQ ID NO: 21 as a result of the Sanger's dideoxy chain termination method. The sequence was determined for all regions of both DNA strands, by overlapping all the section points.

It was confirmed that, from nucleotide number 193 through nucleotide number 642 in the nucleotide sequence shown in SEQ ID NO: 21, there exist an open-reading frame to encode 150 amino acids as described in SEQ ID NO: 22 (FIG. 22). Further, the N-terminal-side amino acid sequence of the protein described in SEQ ID NO: 22 was Met-Ser-Gly-Ala-Arg-Gln-Lys-Lys-Arg-Arg. This sequence was confirmed to correspond to the N-terminal-side amino acid sequence of the above protein, determined beforehand by the amino acid sequencing.

Incidentally, a DNA including the nucleotide sequence consisting of nucleotide numbers 193 to 642 shows 46% homology to the gene of a hypothetical protein of *Bradyrhizobium japonicum* (hereinafter, sometimes referred to as UNK 2) at the amino acid sequence level, and shows 50% homology to the gene of *Mesorhizobium loti* at the amino acid sequence level, from which, it was estimated that the gene was encoding a protein. However, the function of the protein has not been revealed, and it is not at all known whether the gene is involved in the function of promoting growth in the presence of a high concentration of acetic acid.

7. Regarding Spot AAR7

The above cloned Sau3AI fragment was inserted into the BamHI site of pUC19, and the nucleotide sequence of the fragment was determined to be the nucleotide sequence described in SEQ ID NO: 25 as a result of the Sanger's dideoxy chain termination method. The sequence was determined for all regions of both DNA strands, by overlapping all the section points.

It was confirmed that, from nucleotide number 228 through nucleotide number 773 in the nucleotide sequence shown in SEQ ID NO: 25, there exists an open-reading frame to encode 182 amino acids as described in SEQ ID NO: 26 (FIG. 26). Further, the N-terminal-side amino acid sequence of the protein described in SEQ ID NO: 26 was Met-Glu-Tyr-Pro-Met-Ser-Asp-Leu-Ile-Val. This sequence was confirmed to correspond to the N-terminal-side amino acid sequence of the above protein, determined beforehand by the amino acid sequencing.

Incidentally, a DNA including the nucleotide sequence consisting of nucleotide numbers 228 to 773 shows 61% homology to the gene of a hypothetical protein of *Agrobacterium tumefaciens* (hereinafter, sometimes referred to as UNK3) at the amino acid sequence level, and shows 66% homology to the gene of *Shinorhizobium meliloti* at the amino acid sequence level, from which, it was estimated that the gene was encoding a protein. However, the function of the protein has not been revealed, and it is not at all known whether the gene is involved in the function of promoting growth in the presence of a high concentration of acetic acid.

Example 2

Effect of Promoting Growth in a Transformant Transformed with a Gene Having a Function of Promoting Growth, Derived from *Gluconacetobacter entanii* (Part 1)

(1) Transformation of *Acetobacter aceti*

Among DNA fragments derived from *Acetobacter* altoacetigenes MH-24 strain (FERM BP-491), cloned as stated above, an DNA obtained in spot AAR1 was amplified by the PCR method using KOD PLUS™ (Toyobo), and the amplified DNA fragments were inserted into the restriction enzyme SmaI-cleavage site of an acetic acid *Escherichia coli* shuttle vector pGI18, to prepare plasmid pPPI. FIG. 1 shows a schematic of the amplified fragment inserted into the plasmid.

The PCR method was specifically performed as follows. That is, a PCR was performed using the genome DNA of *Acetobacter* altoacetigenes MH-24 strain as a template, and primer 1 (its nucleotide sequence is shown in FIG. 3) and primer 2 (its nucleotide sequence is shown in FIG. 4) as a primer, and also using KOD PLUS™ KOD Plus (Toyobo), under the PCR condition of 30 cycles, each cycle comprising: 94° C., 15 seconds; 60° C., 30 seconds; and 68° C., 30 seconds.

This pPPI was transformed into *Acetobacter aceti* No. 1023 strain by the electroporation method (for example, see Proceedings of the National Academy of Sciences of the United states of America, vol. 87, pp. 8130-8134, 1900). The transformant was selected on a YPG agar medium added with 100 µg/ml ampicillin and 1% acetic acid. A plasmid was extracted by a conventional method and analyzed with respect to an ampicillin-resistant transformant grown on a selective medium. It was confirmed that the transformant retains a plasmid possessing a gene having a function of promoting growth.

(2) The Function of Promoting Growth of a Transformant

A comparison was made based on the growth on an acetic acid-added YPG medium, between the ampicillin-resistant transformant having a plasmid obtained as stated above and the original strain to which only shuttle vector pGI18 was introduced.

Specifically, to a 100 ml of YPG medium containing 3% ethanol, 3% acetic acid, and 100 µg/ml ampicillin, 2 strains each of the transformant and the original strain having shuttle vector pGI18 were inoculated. A shaking-culture was performed at 30° C. (150 rmp) and a comparison was made between the transformants and the original strains with respect to the growth on the acetic acid-added medium, based on the average of absorbance values measured at 660 nm.

Consequently, as shown in FIG. 29, it was confirmed that the transformants were capable of growing, while the original strains were not capable of growing. This confirmed that the DNA obtained in spot AAR1 has a function of promoting growth.

Example 3

Effect of Promoting Growth in a Transformant Transformed with a Gene Having a Function of Promoting Growth, Derived from *Gluconacetobacter entanii* (Part 2)

Plasmid pSOD was produced in the same manner as in Example 2 except that the DNA obtained in spot AAR2 was used, and primer 3 (its nucleotide sequence is shown in FIG. 7) and primer 4 (its nucleotide sequence is shown in FIG. 8)

were used as a primer. FIG. 5 shows a schematic of the amplified fragment inserted into the plasmid.

In the same manner as in Example 2, this pSOD was transformed into *Acetobacter aceti* No. 1023 strain by the electroporation method, and the transformant was confirmed to be retaining a plasmid possessing a gene having a function of promoting growth. Subsequently, in the same manner as in Example 2, a comparison was made between the transformant and the original strain with respect to the growth on the acetic acid-added medium, based on the average of the absorbance values measured at 660 nm. Consequently, as shown in FIG. 30, it was confirmed that the transformants were capable of growing, while the original strains were not capable of growing. This confirmed that the DNA obtained in spot AAR2 has a function of promoting growth.

Example 4

Effect of Promoting Growth in a Transformant Transformed with a Gene Having a Function of Promoting Growth, Derived from *Gluconacetobacter entanii* (Part 3)

Plasmid pUNK was prepared in the same manner as in Example 2 except that the DNA obtained in spot AAR3 was used, and primer 5 (its nucleotide sequence is shown in FIG. 11) and primer 6 (its nucleotide sequence is shown in FIG. 12) were used as a primer. FIG. 9 shows a schematic of the amplified fragment inserted in the plasmid.

In the same manner as in Example 2, this pUNK was transformed into *Acetobacter aceti* No. 1023 strain by the electroporation method, and the transformant was confirmed to be retaining the plasmid possessing the gene having a function of promoting growth. Subsequently, in the same manner as in Example 2, a comparison was made between the transformant and the original strain with respect to the growth on the acetic-acid added medium, based on the average of absorbance values measured at 660 nm. Consequently, as shown in FIG. 31, it was confirmed that the transformants were capable of growing, while the original strains were not capable of growing. This confirmed that the DNA obtained in spot AAR3 has a function of promoting growth.

Example 5

Effect of Promoting Growth in a Transformant Transformed with a Gene Having a Function of Promoting Growth, Derived from *Gluconacetobacter entanii* (Part 4)

(1) Transformation into *Acetobacter aceti*

Plasmid pYBH was prepared in the same manner as in Example 2 except that the DNA obtained in spot AAR4 was used, and primer 7 (its nucleotide sequence is shown in FIG. 15) and primer 8 (its nucleotide sequence is shown in FIG. 16) were used as a primer. FIG. 13 shows a schematic of the amplified fragment inserted into the plasmid.

In the same manner as in Example 2, this pYBH was transformed into *Acetobacter aceti* No. 1023 strain by the electroporation method, and the transformant was confirmed to be retaining the plasmid possessing the gene having a function of promoting growth. Subsequently, in the same manner as in Example 2, a comparison was made between the transformant and the original strain with respect to the growth on the acetic-acid added medium, based on the average of absorbance values measured at 660 nm. Consequently, as shown in FIG. 32, it was confirmed that the transformants were capable of growing, while the original strains were not capable of growing. This confirmed that the DNA obtained in spot AAR4 has a function of promoting growth.

Example 6

Effect of Promoting Growth in a Transformant Transformed with a Gene Having a Function of Promoting Growth, Derived from *Gluconacetobacter entanii* (Part 5)

Plasmid pAHR was prepared in the same manner as in Example 2 except that the DNA obtained in spot AAR5 was used, and primer 9 (its nucleotide sequence is shown in FIG. 19) and primer 10 (its nucleotide sequence is shown in FIG. 20) were used as a primer. FIG. 17 shows a schematic of the amplified fragment inserted into the plasmid.

In the same manner as in Example 2, this pAHR was transformed into *Acetobacter aceti* No. 1023 strain by the electroporation method, and the transformant was confirmed to be retaining the plasmid possessing the gene having a function of promoting growth. Subsequently, in the same manner as in Example 2, a comparison was made between the transformant and the original strain with respect to the growth on the acetic-acid added medium, based on the average of absorbance values measured at 660 nm. Consequently, as shown in FIG. 33, it was confirmed that the transformants were capable of growing, while the original strains were not capable of growing. This confirmed that the DNA obtained in spot AAR5 has a function of promoting growth.

Example 7

Effect of Promoting Growth in a Transformant Transformed with a Gene Having a Function of Promoting Growth, Derived from *Gluconacetobacter entanii* (Part 6)

Plasmid pUNK2 was prepared in the same manner as in Example 2 except that the DNA obtained in spot AAR6 was used, and primer 11 (its nucleotide sequence is shown in FIG. 23) and primer 12 (its nucleotide sequence is shown in FIG. 24) were used as a primer. FIG. 21 shows a schematic of the amplified fragment inserted into the plasmid.

In the same manner as in Example 2, this pUNK2 was transformed into *Acetobacter aceti* No. 1023 strain by the electroporation method, and the transformant was confirmed to be retaining the plasmid possessing the gene having a function of promoting growth. Subsequently, in the same manner as in Example 2, a comparison was made between the transformant and the original strain with respect to the growth on the acetic-acid added medium, based on the average of absorbance values measured at 660 nm. Consequently, as shown in FIG. 34, it was confirmed that the transformants were capable of growing, while the original strains were not capable of growing. This confirmed that the DNA obtained in spot AAR6 has a function of promoting growth.

Example 8

Effect of Promoting Growth in a Transformant Transformed with a Gene Having a Function of Promoting Growth, Derived from *Gluconacetobacter entanii* (Part 7)

Plasmid pUNK3 was prepared in the same manner as in Example 2 except that the DNA obtained in spot AAR7 was used, and primer 13 (its nucleotide sequence is shown in FIG. 27) and primer 14 (its nucleotide sequence is shown in FIG. 28) were used as a primer. FIG. 25 shows a schematic of the amplified fragment inserted into the plasmid.

In the same manner as in Example 2, this pUNK3 was transformed into *Acetobacter aceti* No. 1023 strain by the electroporation method, and the transformant was confirmed to be retaining the plasmid possessing the gene having a function of promoting growth. Subsequently, in the same manner as in Example 2, a comparison was made between the transformant and the original strain with respect to the growth on the acetic acid-added medium, based on the average of absorbance values measured at 660 nm. Consequently, as shown in FIG. 35, it was confirmed that the transformants were capable of growing, while the original strains were not capable of growing. This confirmed that the DNA obtained in spot AAR7 has a function of promoting growth.

INDUSTRIAL APPLICABILITY

According to the present invention, microorganisms can be conferred and enhanced a function of promoting growth in the presence of acetic acid. Therefore, in microorganisms having an alcohol-oxidation capability, particularly in acetic acid bacteria, the function of promoting growth in the presence of acetic acid is improved and the growth-induction period is significantly reduced, whereby acetic acid bacteria can be provided with an ability to accumulate efficiently a high concentration of acetic acid in a culture medium.

The invention claimed is:

1. An isolated protein consisting of the amino acid sequence shown in SEQ ID NO: 2, 6, 14, 18, 22, or 26.

2. An isolated DNA that encodes a protein consisting of the amino acid sequence shown in SEQ ID NO: 2, 6, 14, 18, 22, or 26.

3. An isolated DNA consisting of one of the following nucleotide sequences:
   the nucleotide sequence of nucleotide numbers 213 to 764 in the nucleotide sequence shown in SEQ ID NO: 1;
   the nucleotide sequence of nucleotide numbers 231 to 836 in the nucleotide sequence shown in SEQ ID NO: 5;
   the nucleotide sequence of nucleotide numbers 240 to 731 in the nucleotide sequence shown in SEQ ID NO: 13;
   the nucleotide sequence of nucleotide numbers 201 to 761 in the nucleotide sequence shown in SEQ ID NO: 17;
   the nucleotide sequence of nucleotide numbers 193 to 642 in the nucleotide sequence shown in SEQ ID NO: 21; and
   the nucleotide sequence of nucleotide numbers 228 to 773 in the nucleotide sequence shown in SEQ ID NO: 25.

4. A recombinant vector comprising one or more DNAs selected from DNAs according to any one of claims 2 or 3.

5. A transformant containing the recombinant vector according to claim 4.

* * * * *